(12) United States Patent
Kagawa et al.

(10) Patent No.: US 7,973,291 B2
(45) Date of Patent: Jul. 5, 2011

(54) ELECTRONIC APPARATUS

(75) Inventors: Toshiaki Kagawa, Nara (JP); Hiroshi Doshohda, Chiba (JP)

(73) Assignee: Sharp Kabushiki Kaisha, Osaka (JP)

( * ) Notice: Subject to any disclaimer, the term of this patent is extended or adjusted under 35 U.S.C. 154(b) by 524 days.

(21) Appl. No.: 12/042,134

(22) Filed: Mar. 4, 2008

(65) Prior Publication Data

US 2008/0217556 A1 Sep. 11, 2008

(30) Foreign Application Priority Data

Mar. 7, 2007 (JP) .................................. 2007-057871
Jun. 19, 2007 (JP) .................................. 2007-161907

(51) Int. Cl.
*H01J 27/00* (2006.01)
(52) U.S. Cl. ...................... 250/423 R; 250/281; 361/231
(58) Field of Classification Search ............... 250/423 R
See application file for complete search history.

(56) References Cited

U.S. PATENT DOCUMENTS

| | | | |
|---|---|---|---|
| 3,977,848 A | | 8/1976 | Oliphant |
| 4,040,731 A | | 8/1977 | Nishikawa |
| 4,401,385 A | | 8/1983 | Katayama et al. |
| 4,812,711 A | * | 3/1989 | Torok et al. ............... 315/111.91 |
| 5,047,892 A | * | 9/1991 | Sakata et al. ................... 361/231 |
| 5,521,383 A | | 5/1996 | Furukawa et al. |
| 5,742,874 A | | 4/1998 | Koshimura et al. |
| 6,103,190 A | | 8/2000 | Tanimura et al. |
| 6,235,090 B1 | | 5/2001 | Bernstein et al. |
| 6,373,680 B1 | | 4/2002 | Riskin |
| 6,577,828 B1 | | 6/2003 | Ramos |
| 7,116,394 B2 | * | 10/2006 | Bakker et al. ..................... 355/30 |
| 7,120,006 B2 | * | 10/2006 | Sekoguchi et al. ........... 361/230 |
| 7,199,993 B2 | | 4/2007 | Kato et al. |
| 7,679,879 B2 | * | 3/2010 | Furuhashi et al. ............ 361/231 |
| 2003/0072675 A1 | | 4/2003 | Takeda et al. |
| 2005/0077103 A1 | | 4/2005 | Ikeda et al. |
| 2005/0238381 A1 | | 10/2005 | Song et al. |
| 2005/0271414 A1 | | 12/2005 | Katayama et al. |
| 2007/0212111 A1 | | 9/2007 | Kagawa et al. |
| 2008/0130190 A1 | | 6/2008 | Shimada |

FOREIGN PATENT DOCUMENTS

| | | |
|---|---|---|
| JP | 61-275877 | 12/1986 |
| JP | 2002-95731 A | 4/2002 |
| JP | 2002-268483 | 9/2002 |
| JP | 2004-164918 A | 6/2004 |

(Continued)

OTHER PUBLICATIONS

U.S. Appl. No. 12/042,511, filed Mar. 5, 2008, entitled "Ozone Removal Device, Image Forming Apparatus Having the Same, and Method for Removing Ozone".

*Primary Examiner* — Phillip A Johnston
(74) *Attorney, Agent, or Firm* — Nixon & Vanderhye PC

(57) ABSTRACT

An electronic apparatus of the present invention includes an ion generator which generates ions in an atmosphere to remove chemical emission such as VOC and odor. The ion generator is arranged inside the duct which leads the chemical emission generated from the fixing unit to the discharge opening, and also generates positive ions and negative ions in the atmosphere, thereby can efficiently remove the chemical emission. With this arrangement, an electronic apparatus is realized which sufficiently suppresses the chemical emission such as VOC and odor, and is less likely to dirty the surroundings of the electronic apparatus such as the outer surface thereof and the walls surrounding the electronic apparatus.

14 Claims, 29 Drawing Sheets

FOREIGN PATENT DOCUMENTS

| | | |
|---|---|---|
| JP | 2004-233618 | 8/2004 |
| JP | 2004-319183 A | 11/2004 |
| JP | 2005-4144 | 1/2005 |
| JP | 2005-55515 | 3/2005 |
| JP | 2005-56607 A | 3/2005 |
| JP | 2005-65838 A | 3/2005 |
| JP | 2005-149901 A | 6/2005 |
| JP | 2005-316366 A | 11/2005 |
| JP | 2006-39168 A | 2/2006 |
| JP | 2007-47496 | 2/2007 |
| JP | 2008-52065 A | 3/2008 |
| KR | 2001-0100367 A | 11/2001 |

* cited by examiner

ELECTRONIC APPARATUS

This Nonprovisional application claims priority under 35 U.S.C. §119(a) on Patent Applications No. 057871/2007 filed in Japan on Mar. 7, 2007 and No. 161907/2007 filed in Japan on Jun. 19, 2007, the entire contents of which are hereby incorporated by reference.

FIELD OF THE TECHNOLOGY

The present technology relates to an electronic apparatus (for example personal computers, copiers, printers and the like) which generates chemical emission such as an odor or a VOC (Volatile Organic Compounds). More particularly, the technology relates to an electronic apparatus provided with an ion generation section to reduce the amount of the chemical emission.

BACKGROUND OF THE TECHNOLOGY

Recently, VOC is recognized as one causative agent for so-called sick house syndrome, which causes pollution related health damage such as headaches and dizziness. It is found that this VOC is emitted from electronic apparatuses such as personal computers, copier, printers and the like. For image forming apparatuses among the electronic apparatuses such as copiers and printers, the peculiar odor which generates from heated paper and toner is also a problem, together with the VOC.

In Patent Document 1 (Japanese Unexamined Patent Publication, Tokukai, No. 2005-55515 (Published on Mar. 3, 2005)), a proposal in technology is made towards the problem of the generation of chemical emission such as the VOC or odor as follows: a negative ion generator is provided around the paper output opening provided on the outside of a housing of the image forming apparatus, and the harmful chemical emission being discharged with the paper is decomposed and made harmless by a negative ion. Additionally, the Patent Document 1 discloses a technology providing an odor sensor outside the housing of the image forming apparatus together with the negative ion generator, in which the ON and OFF of the negative ion generator is controlled in accordance with a detection signal from the odor sensor.

However, there are a few problems with the conventional art as described below.

One is that the distance which the negative ion in air can reach from an ion source is limited, for example if there is no wind then the negative ion can only reach up to 100 mm. If the ion generator is provided outside the image forming apparatus (around the transfer paper output opening), the negative ion can only react to the chemical emission discharged and diffused outside the apparatus. The possibility the negative ion would reach the chemical emission is low due to short distance reach of the negative ion, which makes it difficult to effectively reduce the amount of the chemical emission.

Another is that if the negative ion generator is provided outside the housing of the image forming apparatus, the negative ion reacts with nitrogen oxide (NOx) contained in air around the image forming apparatus, causing nitrogen oxide to precipitate outside the housing. This may cause the dirtying of a paper output tray or the housing of the image forming apparatus, or even the wall, floor or the like of the room the image forming apparatus is placed, due to the precipitated nitrogen oxide adhering therewith.

There is also a theory that the negative ion only neutralizes the electric charge of the chemical emission which causes the substance to precipitate, and does not completely decompose and convert the substance to a harmless agent. If the ion generator is provided outside the housing of the image forming apparatus as in Patent Document 1, the once-precipitated VOC may again volatilize (secondary generation), and cause harm.

SUMMARY OF THE TECHNOLOGY

An object is to provide an electronic apparatus which can sufficiently suppress the diffusion of a chemical emission such as a VOC and an odor, and which is less likely to dirty the surroundings of the electronic apparatus such as the outer surface thereof and the walls surrounding the electronic apparatus.

In order to attain the above object, a first electronic apparatus is an electronic apparatus which includes a housing and entails the generation of a chemical emission inside the housing, the electronic apparatus including: an ion generation section, which is arranged inside the housing, for generating ions into an atmosphere to remove the chemical emission from the atmosphere; and a power supply applying an alternating voltage, the ion generation section generating positive ions and negative ions in the atmosphere upon application of an alternating voltage by the power supply.

In order to attain the above object, a second electronic apparatus is an electronic apparatus which includes a housing and entails the generation of a chemical emission inside the housing, the electronic apparatus including: an ion generation section, which is arranged inside the housing, for generating ions into an atmosphere to remove the chemical emission from the atmosphere, wherein the ion generation section includes two ion generation sections, one being a negative ion generation section generating negative ions and the other being a positive ion generation section generating positive ions.

According to the structure of the first and second electronic apparatuses, the ions generated by the ion generation section react with the chemical emission before the substance is discharged and diffused from the housing in this structure. This enables the efficient removal of the chemical emission from the atmosphere. Thus, the chemical emission such as the VOC and odor is sufficiently suppressed, as compared to the electronic apparatus in Patent Document 1.

Additionally, at least some of the ions generated by the ion generation section disappear while moving to the outside of the housing. Therefore, the amount of the ion which will react with nitrogen oxide outside the housing is suppressed. Thus, the surroundings of the electronic apparatus such as the outer surface thereof or the walls surrounding the electronic apparatus are less likely to become dirty.

Moreover, the reaction of the generated ions with the chemical emission occurs mainly within the housing. This prevents inactivated volatile chemical substances inactivated by the reaction from being precipitated outside the housing. Consequently, the re-volatilization of the precipitated chemical emission outside the housing of the electronic apparatus is less likely to occur and harm the human body.

Furthermore, in the structure of the first electronic apparatus, the electrode member alternately holds positive and negative potentials when an alternative voltage is applied to the electrode member. As a result, positive ions and negative ions generate in the atmosphere around the electrode member. Many of the volatile chemical substances such as the odor and VOC are charged positively; however, there are ones that are negatively charged. This structure enables effective removal of the chemical emission, regardless of whether the chemical emission is charged positively or negatively.

DESCRIPTION OF THE EMBODIMENTS

The technology may be applied to various electronic apparatuses which generate the chemical emission.

First Embodiment

Figure 1:
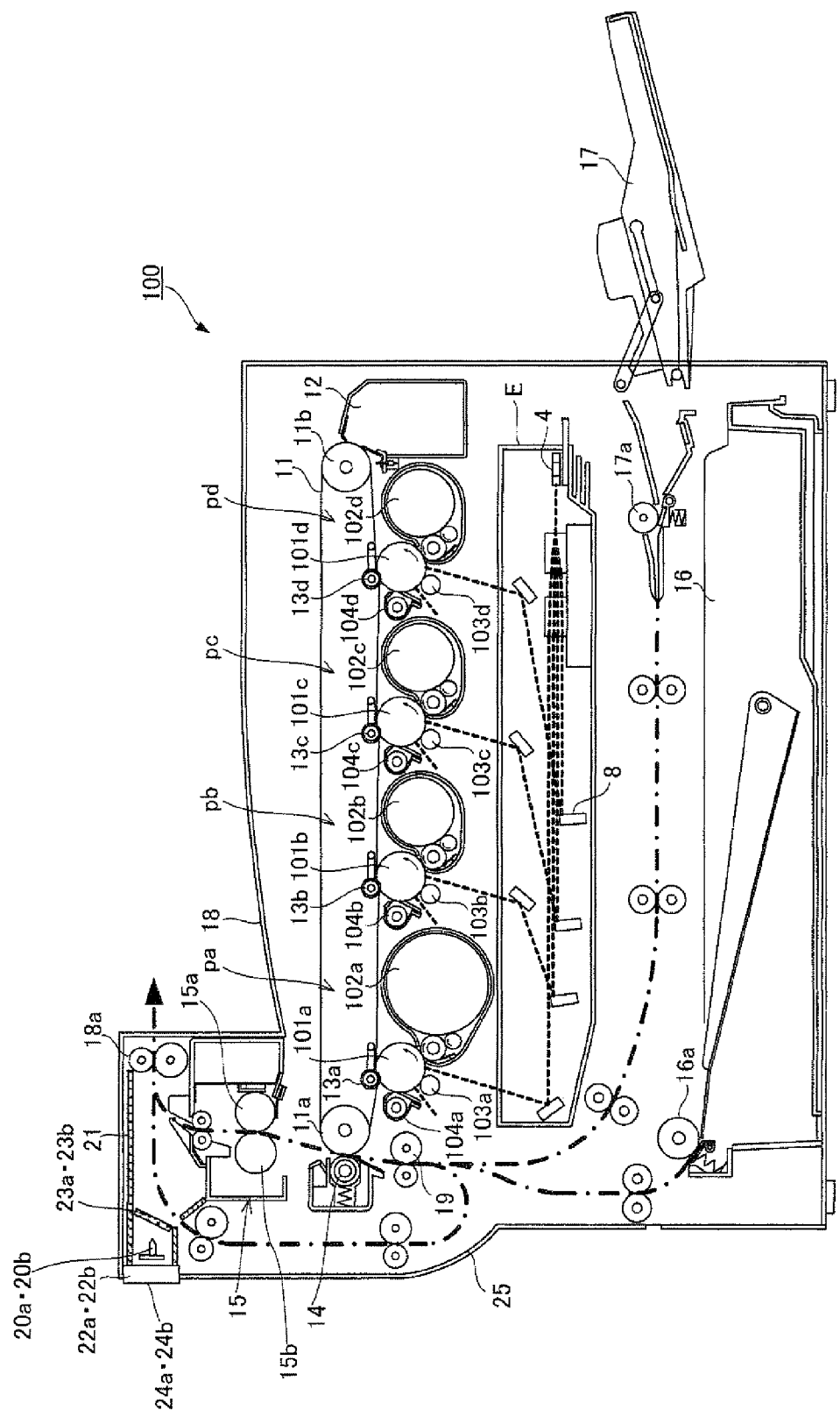
FIG. 1 illustrates a First Embodiment and is a longitudinal sectional view schematically illustrating the structure of a color multifunction apparatus.

The first embodiment is described as below with reference to FIGS. 1 through 9. The present embodiment explains an example applying the technology to a color multifunction apparatus. FIG. 1 illustrates one embodiment of the and is a longitudinal sectional view of a brief structure of a color multifunction apparatus 100.

The color multifunction apparatus 100 is an electrophotographic image forming apparatus. Multicolor or monochrome images are formed on a sheet (recording medium, printing paper) based on a print job data inputted from a personal computer or the like not illustrated. The color multifunction apparatus 100 includes an optical unit E, four visible image formation units pa, pb, pc and pd, an intermediate transfer belt 11, a secondary transfer unit 14, a fixing unit 15, and an inner paper feeding unit 16, which are an image formation section which forms an image on a sheet, a housing 25 containing the image formation section, a manual paper feeding tray 17, a paper output tray 18 and the like, as illustrated in FIG. 1.

The visible image formation unit pa, pb, pc, and pd form a toner image of black (K), yellow (Y), magenta (M), and cyan (C), respectively. The visible image formation unit pa includes a photosensitive drum 101 being the carrier of the toner image, with a developing unit 102a, a charging unit 103a, and a cleaning unit 104a arranged surrounding the photosensitive drum 101.

The charging unit 103a evenly charges the surface of the photosensitive drum 101a to a predetermined potential. The present embodiment adapts the charging unit 103a of a charging roller type, enabling the charging unit 103a to evenly charge the surface of the photosensitive drum 101a with the least amount of ozone being generated. A contact-type brush or a non-contact-type charger may also be used as the charging unit 103a instead of a contact-type roller as illustrated in FIG. 1.

The optical unit E is equipped with a laser radiation section 4 and a reflection mirror 8. The optical unit E exposes light from the laser radiation section 4 to the photosensitive drum 101a, 101b, 101c and 101d in accordance with the inputted print job data, forming an electrostatic latent image on each photosensitive drum. A device for example an EL or LED writing head with an array of light-emitting elements may be adapted as an exposing unit 1 instead of the aforementioned structure.

The developing unit 102a develops the electrostatic latent image formed on the photosensitive drum 101a with toner. The developing unit 102a contains a K toner, and the developing units 102b, 102c, and 102d contain Y, M, and C toners, respectively. A primary transfer unit 13a is arranged on the upper side of the photosensitive drum 101a sandwiching the intermediate transfer belt 11, and transfers the toner image formed on the surface of the photosensitive drum 101a to the intermediate transfer belt 11. The cleaning unit 104a removes and collects the toner remaining on the surface of the photosensitive drum 101a after the transfer step.

The other three visible image formation units pb, pc, and pd are all with the same structure as the visible image formation unit pa.

The intermediate transfer belt 11 is suspended in a tensioned state by the two tension rollers 11a and 11b. A waste toner box 12 is arranged on the tension roller 11b side of the intermediate transfer belt 11 having contact therewith, and the secondary transfer unit 14 is arranged on the tension roller 11a side of the intermediate transfer belt 11 having contact therewith. The fixing unit 15 includes a fixing roller 15a and a pressure roller 15b. The fixing roller 15a and the pressure roller 15b are pressed against each other at a predetermined pressure, by pressure means not illustrated. The fixing unit 15 is arranged downstream from the secondary transfer unit 14 in the paper carriage direction.

The image formation process in the color multifunction apparatus is performed as follows. Firstly, the charging unit 103a evenly charges the surface of the photosensitive drum 101a. The optical unit E radiates with a laser the charged areas of the surface of the photosensitive drum 101a in accordance with the image data, which creates an electrostatic latent image. The developing unit 102a then develops the electrostatic latent image on the photosensitive drum 101a with the toner. The primary transfer unit 13a to which a bias voltage opposite in polarity to the toner is applied, transfers the developed toner image to the intermediate transfer belt 11. The other three visible image formation units pb, pc, and pd also conduct the same operation as above, and consecutively transfer the toner image of each color to the intermediate transfer belt 11 on top of each other.

The toner image on the intermediate transfer belt 11 is carried to the secondary transfer unit 14, and this secondary transfer unit 14 to which the bias voltage opposite in polarity to the toner is applied, transfers the toner image to the printing paper, being carried from either the paper feeding roller 16a of the inner paper feeding unit 16, or a paper feeding roller 17a of a manual paper feeding unit 17. The transferred toner image on the printing paper is carried to the fixing unit 15, and the fixing unit 15 adequately heats and fuses the toner image on the printing paper. The printing paper with the fused toner image is outputted by the paper output roller 18a to the paper output tray 18.

Figure 2:
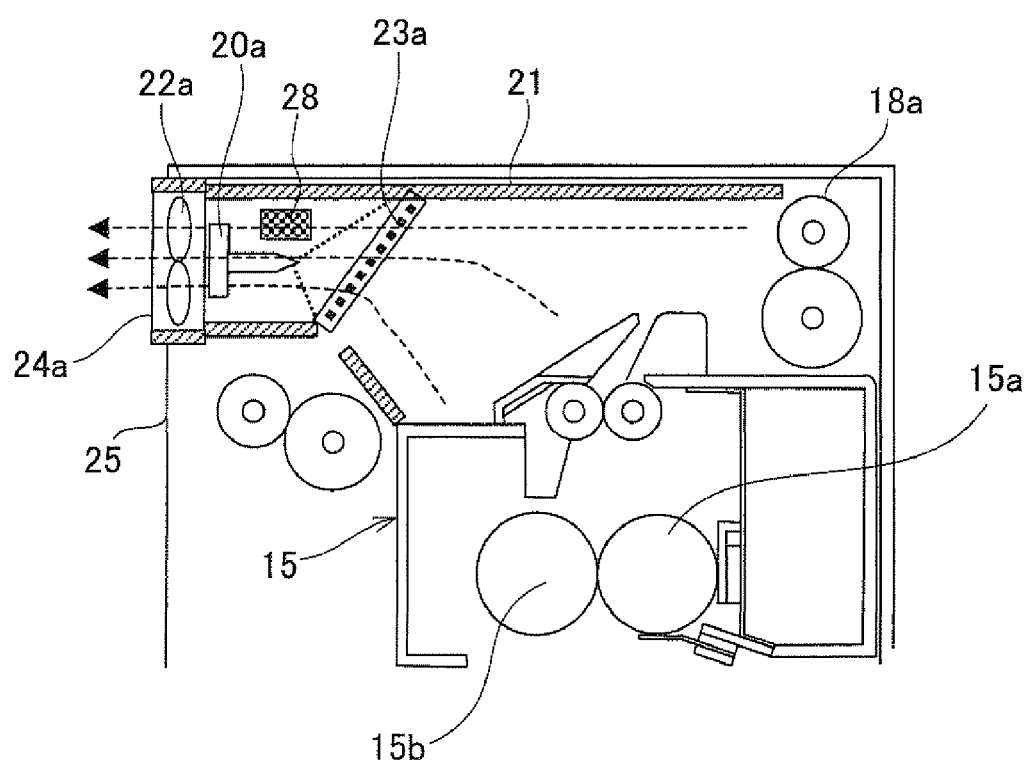
FIG. 2 illustrates a First Embodiment and is an enlarged view of an essential part which is the structure of components around a duct in FIG. 1.
Figure 3:
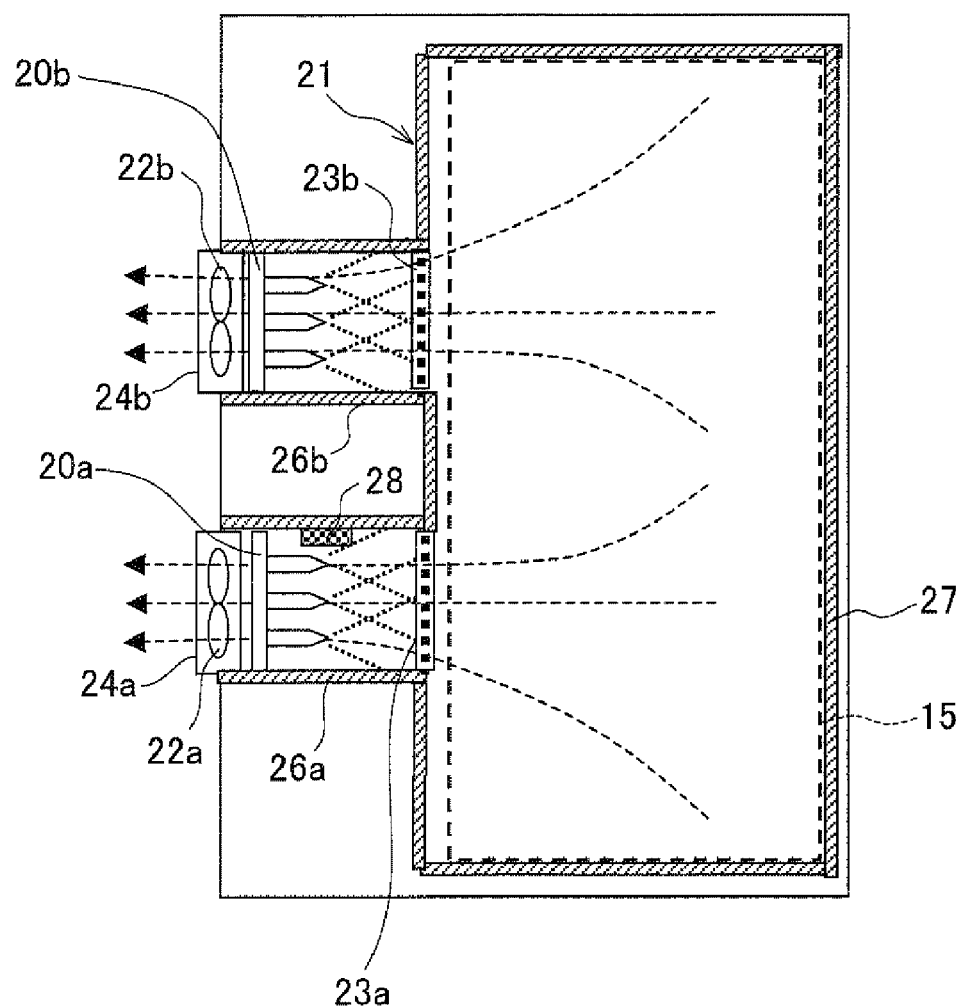
FIG. 3 illustrates a First Embodiment and is a transverse sectional view illustrating the structure of the components around the duct.

In order to prevent the temperature rising inside the housing 25 of the color multifunction apparatus 100, a duct 21 is provided inside the housing 25, on the upper section of the fixing unit 15 in the present embodiment. FIG. 2 is an enlarged view of an essential part of FIG. 1, illustrating a detailed structure around the duct 21. FIG. 3 is a transverse sectional view of the duct 21.

As illustrated in FIG. 2, the duct 21 is adjacent to the fixing unit 15. The duct 21 has a main section 27 arranged above the fixing unit 15 as a bottomless cover, and two hollow cylinder sections 26a and 26b extending from the main section 27. The hollow cylinder sections 26a and 26b communicate respectively with an exhaust opening 24a and 24b provided on the housing 25, the inside forming an air flow passage. The diameters of the hollow cylinder sections 26a and 26b are uniform, and are made in the same size as the diameters of the exhaust openings 24a and 24b.

The hollow cylinder sections 26a and 26b have exhaust fans 22a and 22b provided respectively at the ends thereof facing the exhaust openings 24a and 24b. On the opposite sides of the hollow cylinder sections 26a and 26b (on the main section 27 sides), filters 23a and 23b which remove dust are arranged, respectively, so as to block the air flow passages. The exhaust fans 22a and 22b rotate so as to carry the air inside the hollow cylinder sections 26a and 26b from the main section 27 side to the exhaust openings 24a and 24b side. The air heated by the fixing unit 15 is thus collected at the main section 27 of the duct 21, and is carried from the exhaust openings 24a and 24b to the outside of the housing 25 via the hollow cylinder sections 26a and 26b.

The VOC such as siloxanes or the like generate in the electrophotographic image forming apparatus such as copiers, laser printers and multifunction device and the like, being caused by the heating of a silicon rubber used in the fixing roller and the pressure roller of the fixing unit. In addition, the toner includes components of the VOC or odor, thereby causes the generation of the VOC or odor effected by the melting of the toner by heat application in the fixing process. As such, in the electrophotographic image forming apparatus, most of the VOC or odor is mainly generated around the fixing unit, and the generated VOC or odor is outputted to the outside of the housing together with the heated air being heated in the fixing unit.

In order to remove the generated VOC or odor, the present embodiment arranges an ion generator 20a between the exhaust fan 22a and the filter 23a and an ion generator 20b between the exhaust fan 22b and the filter 23b. In other words, the ion generator 20a and 20b are arranged upstream of the exhaust fans 22a and 22b and downstream of the filters 23a and 23b, in the air carrying direction.

The ion generator 20 generates a negative ion inside the duct 21, which neutralizes the VOC or odor by the reaction therewith. This allows the reduction of the VOC or odor contained in the exhaust air. The present embodiment is arranged such that the chemical emission is effectively removed before the chemical emission is outputted and diffused from the exhaust openings 24a or 24b, by having the negative ion react with the chemical emission inside the duct 21.

Each of the ion generators 20a and 20b may be anything as long as it is able to stably generate a certain amount of negative ions, and may be a corona discharge type ion generator, electronic discharge type ion generator, surface discharge type ion generator or the like ion generator. For the purpose of suppressing the generation of ozone at the least, the present embodiment adapts the electronic discharge type ion generator 20a and 20b, which applies a high voltage to a needle-shaped member without a counter electrode, as illustrated in FIG. 3. The ion generators 20a and 20b are hereinafter referred collectively to as an ion generator 20.

Figure 4:
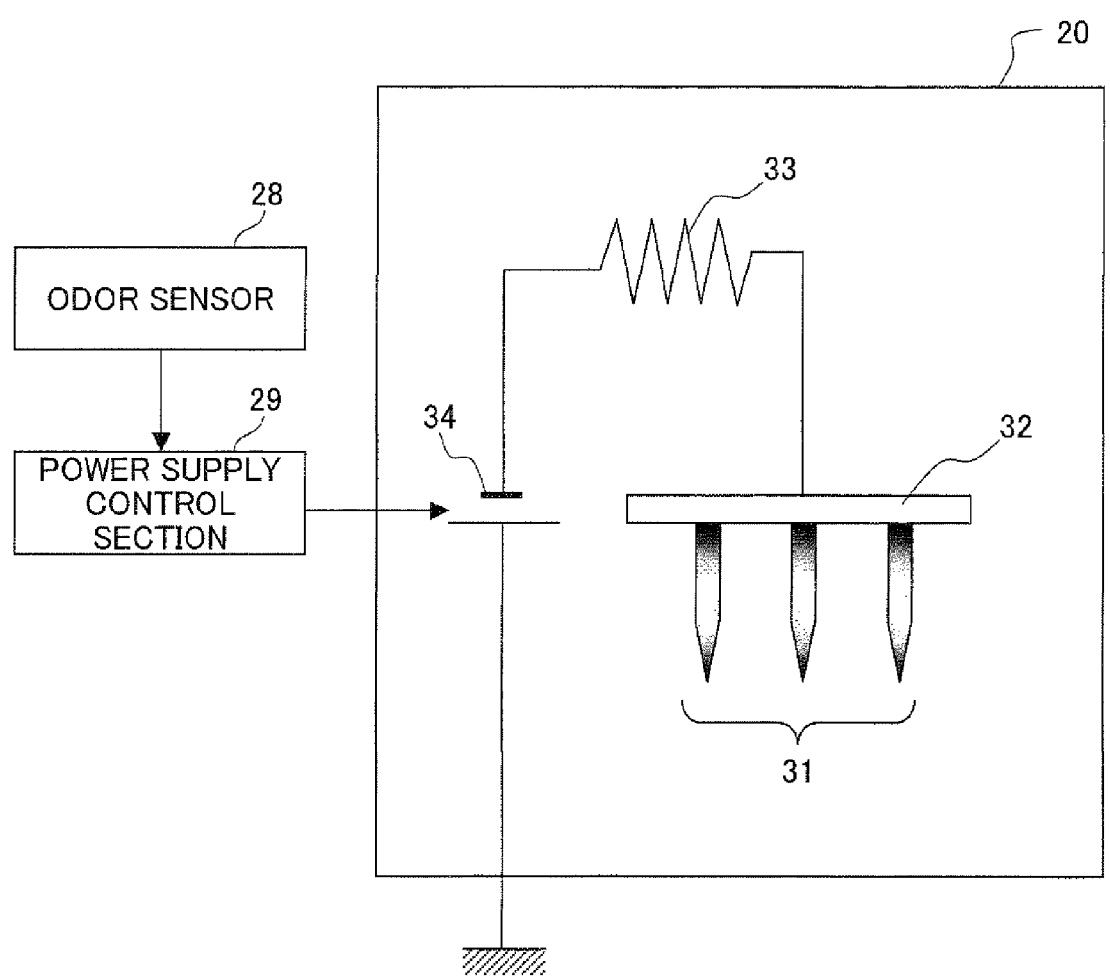
FIG. 4 illustrates one embodiment and is a schematic view of an electronic discharge type ion generator.

FIG. 4 is a side view illustrating the ion generator 20. The ion generator 20 includes a plurality (three in the embodiment) of ionization needles 31, a base frame 32 to support the ionization needles 31, a high voltage power supply 34 to make voltage of the ionization needles 31 higher than that of a ground, and a fixed resistor 33.

Each of the ionization needles 31 is made of a tungsten (purity of 99.999%) in a needle-shape, with a diameter of 1 mm and a curvature radius of a needlepoint of 15 μm. The ionization needles 31 are arranged fixed on the base frame 32 so as to be spaced at a pitch of 10 mm. The base frame 32 is made of metal (stainless steel in the embodiment), and is connected to the negative electrode of the high voltage power supply 34. The positive electrode of the high voltage power supply 34 is grounded. The fixed resistor 33 has a resistance of 200MΩ, and is inserted between the base frame 32 and the high voltage power supply 34. When the high voltage power supply 34 is turned ON, a voltage of −5 kV is applied to each of the ionization needles 31 via the fixed resistor 33. In other words, the ionization needles 31 will have an electrical potential of −5 kV with respect to the ground.

The fixed resistor 33 is inserted in the ion generator 20 in order to suppress the change in impedance of the ion generation space occurring with the change in humidity or the like, and also to suppress the change in electric current caused by the adhering of corona products, toner and/or paper powder on the needlepoint of the ionization needle 31. Thus, the ion is stably generated by the ion generator 20.

As illustrated in FIGS. 2 and 3, the ionization needles 31 of the ion generator 20 are arranged such that the needlepoint faces upstream in the air carrying direction of the duct 21. Thus, the negative ion generated by the ionization needles 31 is dispersed towards the fixing unit 15 inside the housing 25, which enables the efficient removal of the chemical emission generated around the fixing unit 15.

The filter 23 which removes the dust is arranged upstream of the ion generator 20 in the air carrying direction, thereby enables the prevention of dirtying in the ionization needles 31 caused by the toner, paper powder or the like. This enables the amount of ion generation to be stably maintained for a long term.

The present embodiment also provides an odor sensor 28 on the inner wall of the hollow cylinder section 26a of the duct 21, as illustrated in FIGS. 2 and 3. The odor sensor 28 detects the odor included in the atmosphere. For this odor sensor 28, for example an "Odor Level Indicator XP-329 III" manufactured by New Cosmos Electric Co., Ltd may be used.

The color multifunction apparatus 100 further includes a power supply control section 29, which controls the high voltage power supply 34 of the ion generator 20, as illustrated in FIG. 4. The power supply control section 29 turns on the high voltage power supply 34 when the output value of the odor sensor 28 exceeds the predetermined threshold value, and turns off the high voltage power supply 34 when the output value of the odor sensor 28 falls below the predetermined threshold value. This allows the ion generators 20a and 20b to generate the negative ion only when the odor inside the housing 25 of the color multifunction apparatus 100 is strong, whereby extending the life of the ionization needles 31 or the like.

Described below is an experiment performed in order to study the validity of the technology.

Experiment 1

A relationship between a distance from the central ionization needle 31 and a concentration of the negative ion was studied, using the ion generator 20. In details, the concentration of the negative ion in an atmosphere was measured while changing the distance from the ionization needles 31, under the state where: (i) the ion generator 20 was positioned in a space with nothing surrounding within 1 m in all directions, (ii) the base frame 32 was connected to the high voltage power supply 34, and (iii) a voltage of −5 kV was applied to the ionization needles 31.

A MODEL 610C manufactured by Trek Incorporated was used for the high voltage power supply 34, and an AIC-2000 manufactured by Sato Shoji Corporation was used as a negative ion counter. The negative ion counter was arranged such that the air suction opening thereof was positioned 5 to 150 mm away from the needlepoint of the ionization needles 31 and the number of negative ions (number included in an air of a given capacity, corresponding to the ion concentration) was measured by the ion counter.

Figure 5:
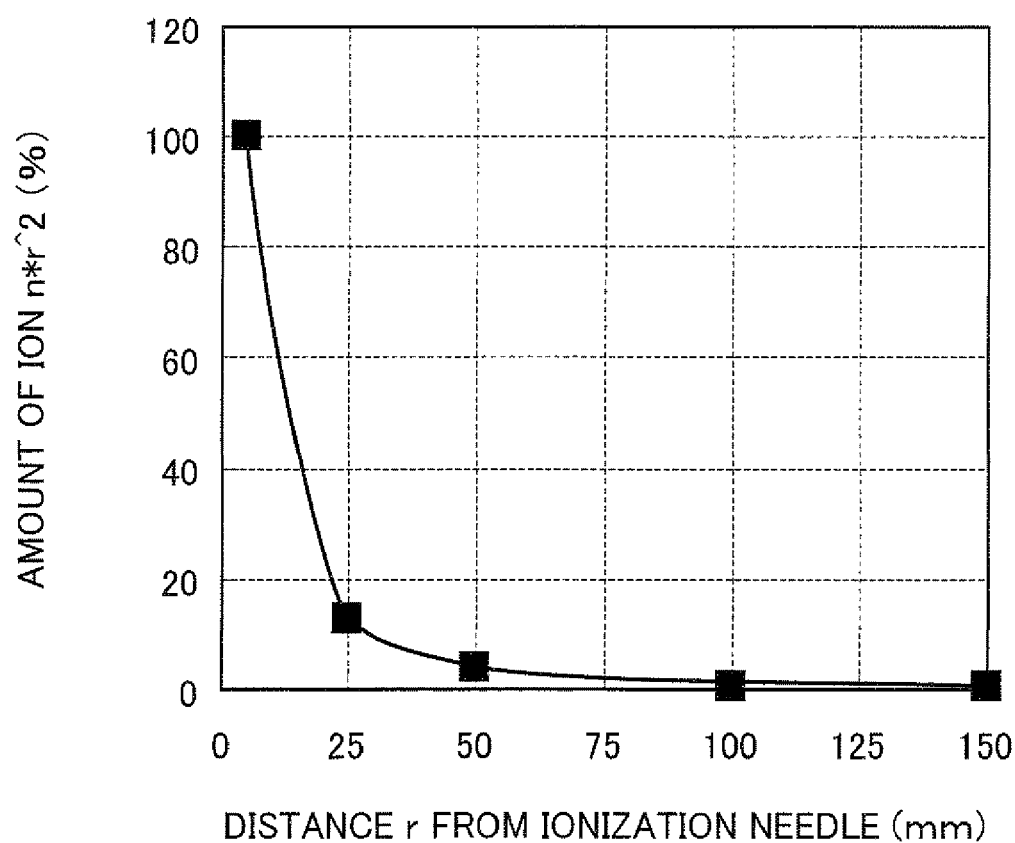
FIG. 5 illustrates the result of Experiment 1, and is a view illustrating relationship between a distance from a needle-point of an ionization needle of the ion generator and the amount of ions.

It is basically conceivable that the ion concentration is inversely proportional to the square of a distance r from the ionization needles 31. This is because the generated ion tends to diffuse more in a farther distance. Accordingly, an $n*r^2$ was calculated, i.e. a value obtained by multiplying the measured number of the negative ions, which is represented by n, by the square of the distance r from the needle point of the ionization needles 31 to the negative ion counter. Next, a percentage of a relative ion amount ($n*r^2$) for each distance was calculated on a base of the $n*r^2$ (100%) obtained when r=5 mm. The calculation result is as illustrated in FIG. 5.

If the generated ion is simply diffused three-dimensionally, the value of $n*r^2$ would be fixed regardless of the distance r. However it is found that actually the value $n*r^2$ decreases as the distance r increases as illustrated in FIG. 5, with a result of hardly any ion reaching a position 100 mm or more away from the ion counter compared to the position 5 mm away therefrom. Possible causes of this are that the generated negative ions link with reversely charged ions (a positive ion in this case) existing in the air, and the distance diffused by the negative ions is limited due to the collision with air molecules.

As such, in order to efficiently reduce the VOC or odor by the negative ion, emitting the negative ions from a close distance towards the VOC or odor is highly preferred. At least, it is considered preferable to arrange the ion generator 20 at the position within 100 mm from the ion generation source (the fixing unit 15 in this case), as conventionally suggested.

Experiment 2

Next, the effect of reducing the VOC or odor by the negative ions generated from the ion generator 20 was studied. The present experiment uses a color laser printer CX-400 manufactured by Ricoh Company, Ltd. instead of the color multifunction apparatus 100, arranging the ion generator 20 in the space above a fixing unit inside the housing thereof. The odor and TVOC (total Volatile Organic Compounds) was measured in the vicinity of the paper output opening after continuous printing with the CX-400. This measurement was repetitively conducted while changing the voltage being applied to the ionization needles 31 of the ion generator 20, in a range of 0V to −3.5 kV. A total of 100 color copies were printed in the continuous printing, with a print rate of 20% (5% per color) at a speed of 25 sheets per minute. An XP-329 III manufactured by New Cosmos Electric Co., Ltd was used as an odor measuring device, and an HV-1000 manufactured by JMS was used as a TVOC measuring device. The measurement result is as illustrated in FIG. 6.

Figure 6:
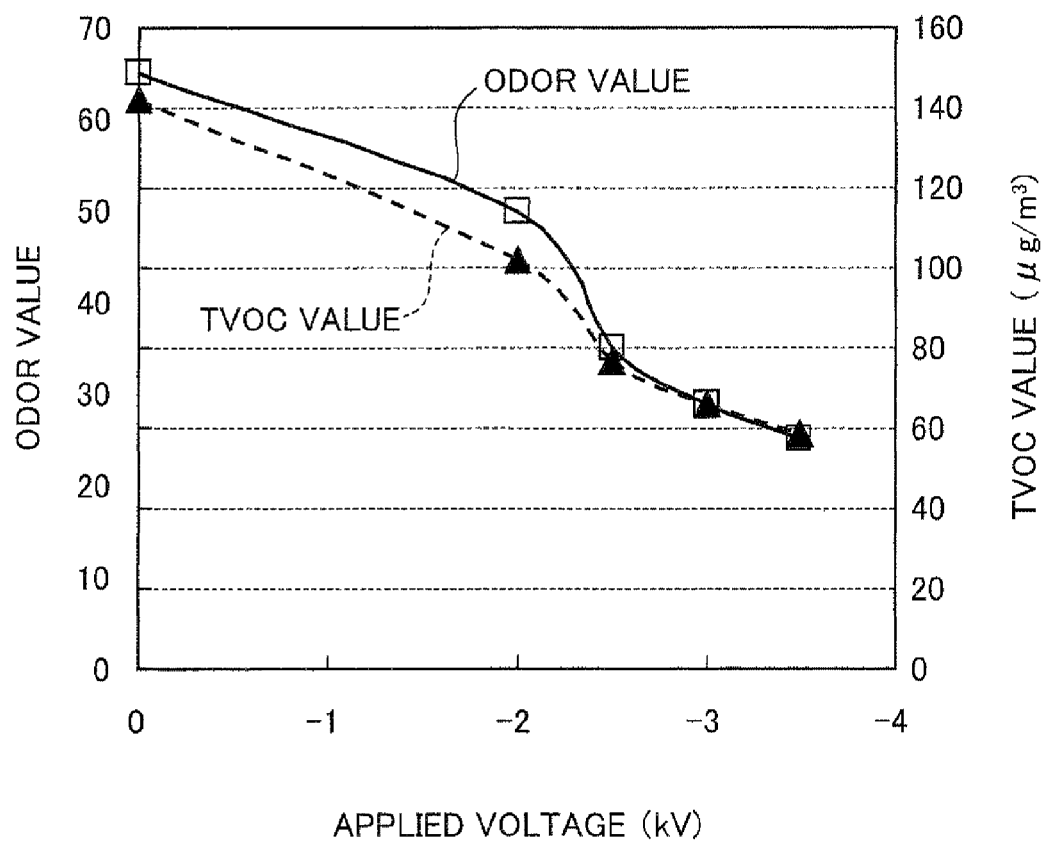
FIG. 6 illustrates the result of Experiment 2, and is a view illustrating relationship between magnitude in voltage applied to the ionization needle of the ion generator and an odor value and a TVOC value.

As illustrated in FIG. 6, the TVOC and the odor in the vicinity of the paper output opening decreased in value with increase in a magnitude (absolute value) of the voltage being applied to the ionization needles 31 of the ion generator 20. Thus, the effect was confirmed that the TVOC and odor are reduced by the negative ions generated from the ion generator 20 arranged above the fixing unit.

Experiment 3

Figure 27:
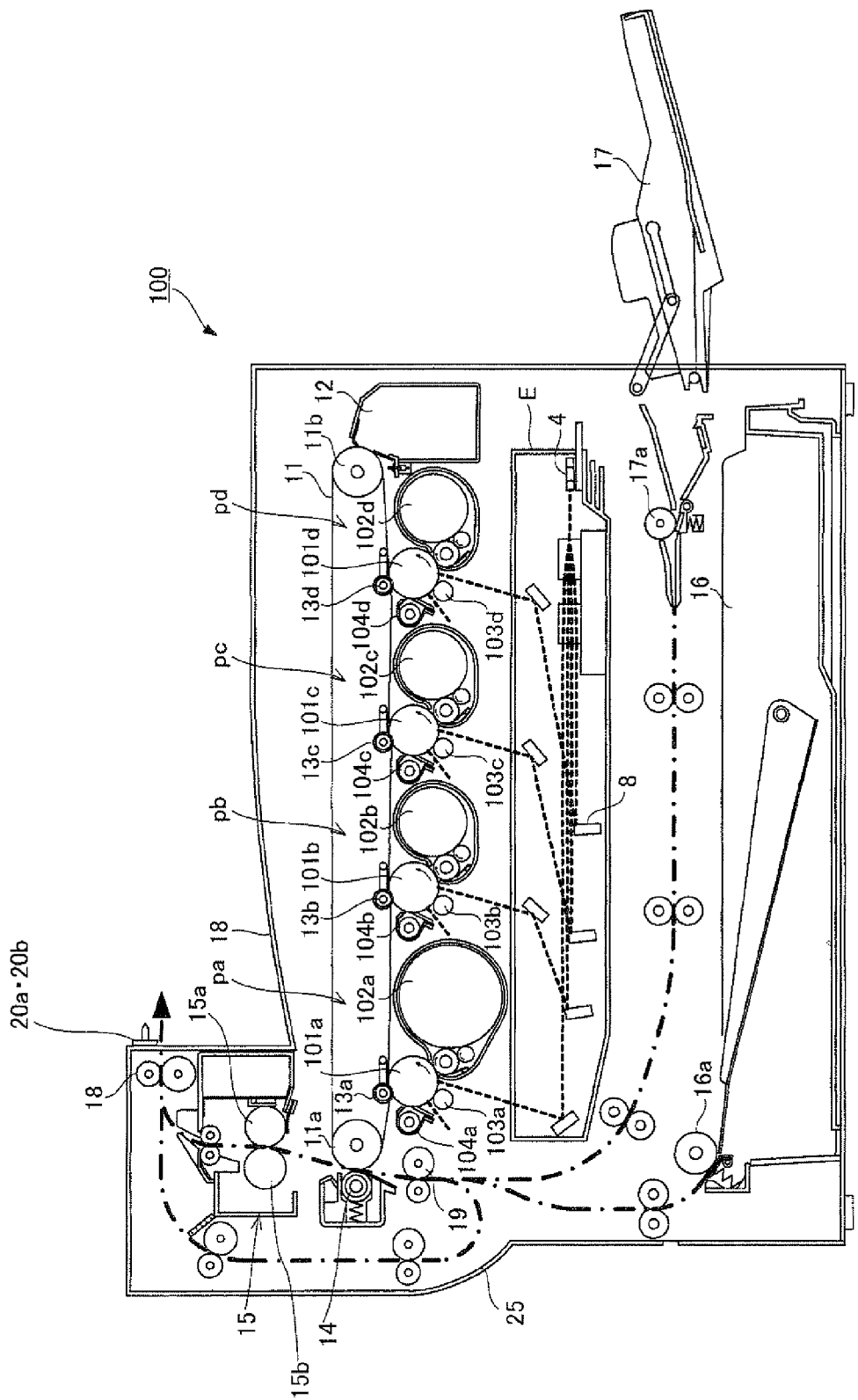
FIG. 27 is a longitudinal sectional view illustrating a brief structure of a color multifunction apparatus used as a comparative example in Experiment 3.

Following is an explanation of the study of the effect attained by arranging the ion generator 20 inside a housing of an apparatus. The comparative experiments were conducted using the following three color multifunction apparatuses: (i) an MX-4500N manufactured by Sharp Corporation, provided with the ion generator 20 inside the duct within the housing, as illustrated in FIG. 1 (Example 1); (ii) an MX-4500N manufactured by same, provided with the ion generator 20 in the vicinity of the paper output opening which is outside the housing, as illustrated in FIG. 27 (Comparative Example 1); and (iii) an MX-4500N manufactured by same, without the ion generator 20 being provided (Comparative Example 2). The filter 23 was not arranged in the Example 1, Comparative Example 1 and Comparative Example 2.

In the present experiment, the color multifunction apparatus of the Example 1, Comparative Example 1 and Comparative Example 2 were placed in a chamber with a capacity of 9.8 $m^3$, and the increasing value of an odor value and TVOC value inside the chamber was measured when a total of 500 color copies were printed with a print rate of 20% (5% per color) at a speed of 35 sheets per minute. The XP-329III manufactured by New Cosmos Electric Co., Ltd was used for the odor measuring device, and the JHV-1000 manufactured by JMS was used for the TVOC measuring device. In addition, a voltage of −10 kV was applied to the ionization needles 31 of the ion generator 20 in Example and Comparative Example 1. The result of the experiment is as illustrated in FIGS. 7 and 8.

Figure 7:
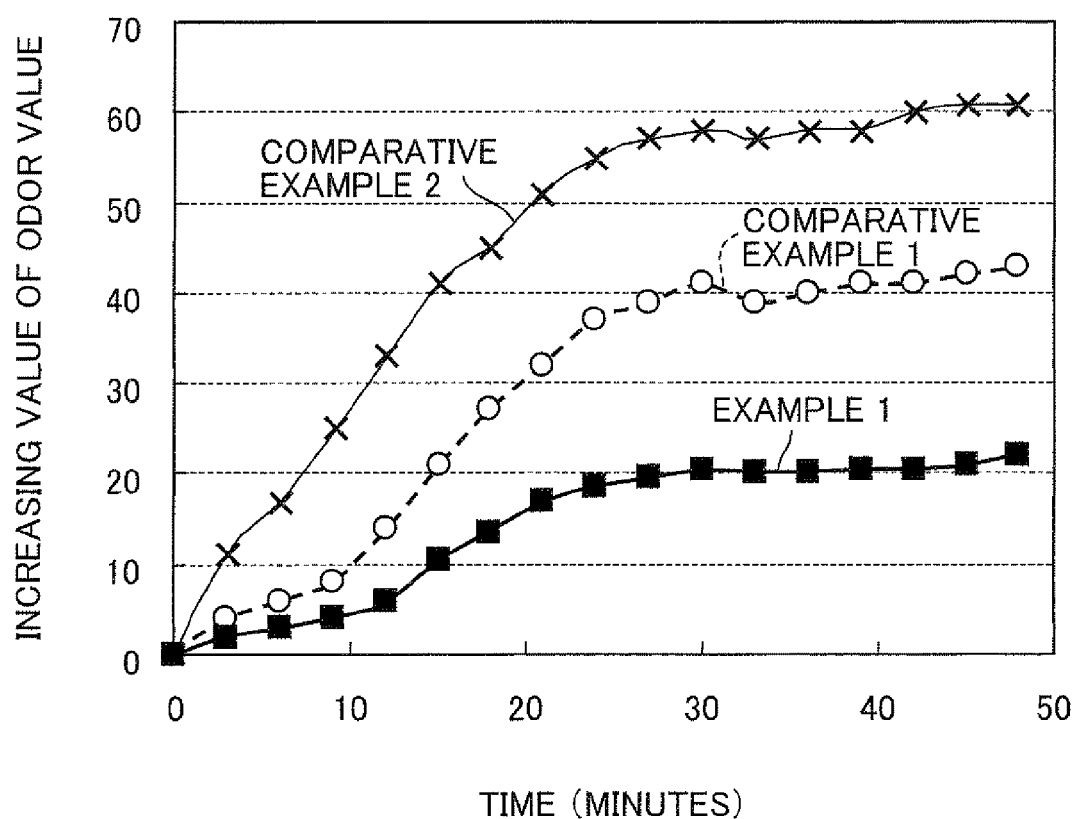
FIG. 7 illustrates the result of Experiment 3, and is a view illustrating relationship between an elapsed time and an increasing value of the odor value.
Figure 8:
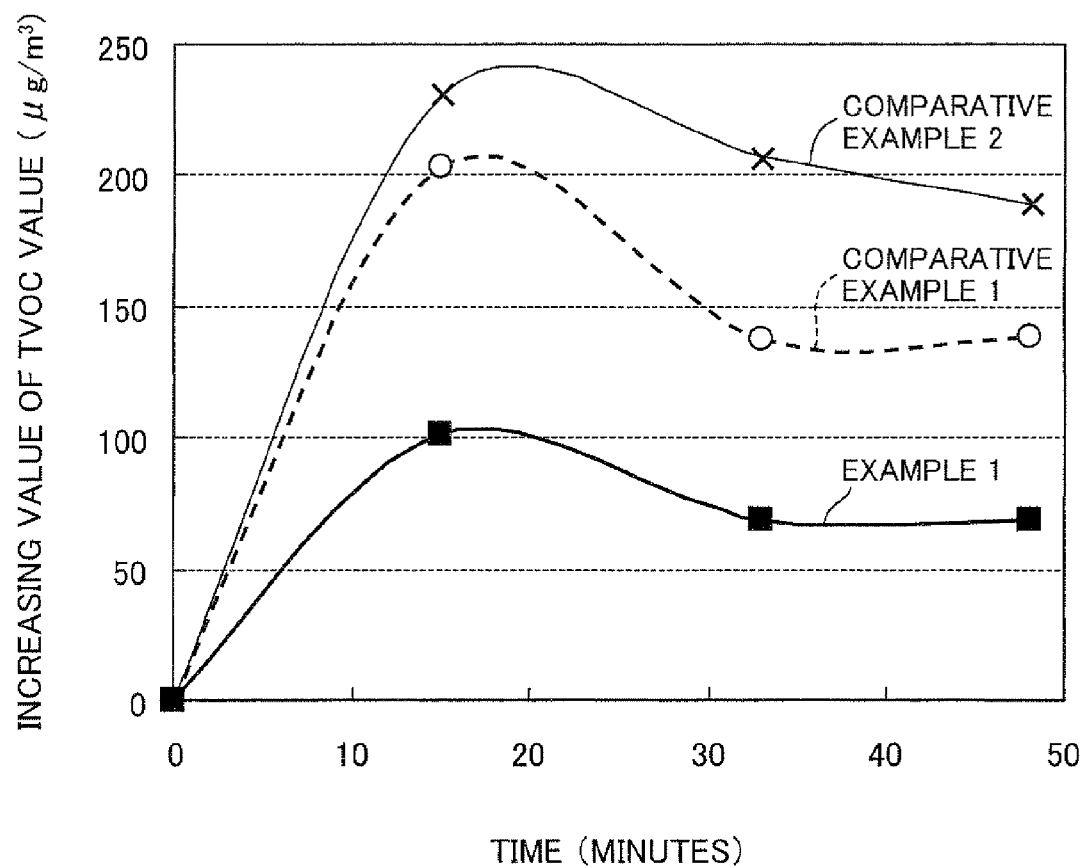
FIG. 8 illustrates the result of Experiment 3, and is a view illustrating relationship between the elapsed time and an increasing value of the TVOC value.

As illustrated in FIGS. 7 and 8, it is confirmed that the odor and VOC reduce in value by provision of the ion generator 20. It is also made clear that the reduction effect of the VOC and odor inside the chamber is greater in the Example 1 with the ion generator 20 provided within the housing (inside the duct), compared to the Comparative Example 1 with the ion generator 20 provided outside of the housing.

A possible cause of the experimental result is that the ions generated by the ion generator 20, which cannot diffuse in a broad range as indicated in Experiment 1, cannot effectively react with the VOC and odor being broadly diffused inside the chamber, if the ion generator 20 is provided outside the housing of the device.

As such, the ion generator 20 is preferably provided inside the housing 25, as in the color multifunction apparatus 100. Furthermore, it is even more preferable to arrange the ion generator 20 inside the duct 21 which discharges the air around the fixing unit 15 to the outside, whereby enables the negative ions to react with the chemical emission of a higher concentration.

If the ion generator 20 is arranged inside the housing, the negative ions are continuously supplied to the chemical emission deposited inside the housing. Therefore, it is less likely for the once deposited chemical emission to volatilize again, compared to the case for the ion generator 20 provided outside of the housing.

In addition, in the Comparative Example 2 with the ion generator 20 provided outside of the housing, certain areas such as the inner wall of the chamber which is near the discharge opening and the packaging of the color multifunction apparatus blackened. This was not recognized with the Example 1. A possible cause of this is as follows: If the ion generator 20 is provided outside the housing, the generated ion reacts with the NOx contained in the air outside of the housing, which causes the adhering of a product generated by the reaction of the negative ion and the NOx on the surrounding walls and floor, and also the packaging of the color multifunction apparatus. If the ion generator 20 is provided inside the housing, most of this reaction and adhering would only occur inside the housing.

As such, the experiment concludes that the ion generator 20 is preferably provided inside the housing of the color multifunction apparatus, also from the point in preventing the dirtying of the surrounding walls and floor of the color multifunction apparatus, or the packaging parts such as the housing of the color multifunction apparatus.

(Modification)

Described below is a modification of the color multifunction apparatus 100 of the present embodiment. The aforementioned color multifunction apparatus 100 is arranged such that the power supply control section 29 controls the high voltage power supply 34 of the ion generator 20 according to the detection result of the odor sensor 28. However a VOC sensor which detects the VOC may be used instead of the odor sensor 28 which detects the odor.

Figure 9:
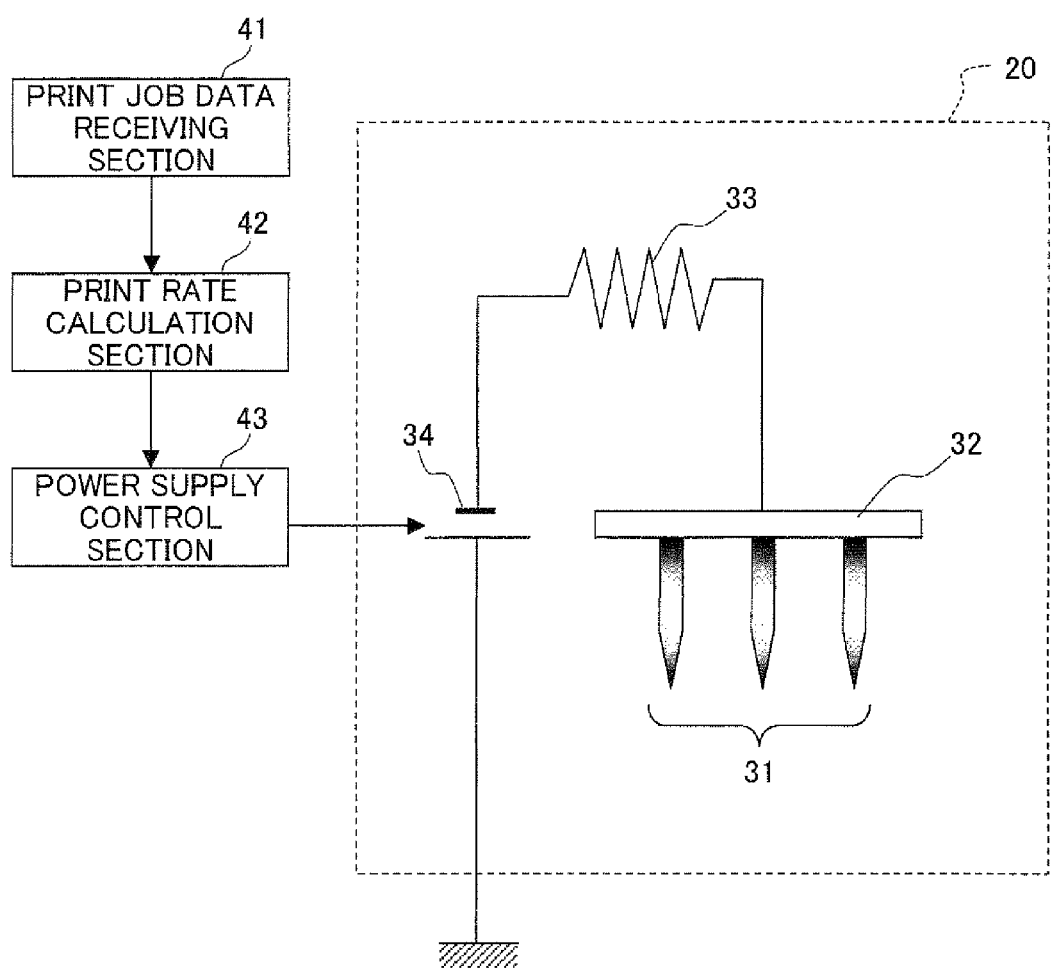
FIG. 9 illustrates modification of a First Embodiment, and is a view illustrating the structure for control of the voltage applied to the ionization needle.

The power supply control section 29 may also adjust the voltage that the high voltage power supply 34 applies to the ionization needles 31 according to the print rate being calculated from the print job data acquired or created by the color multifunction apparatus 100. FIG. 9 is a block diagram illustrating the control mechanism of the high voltage power supply 34 in the present modification. The color multifunction apparatus 100 includes a print job data receiving section 41, a print rate calculation section 42, and a power supply control section 43, as illustrated in FIG. 9.

The print job data receiving section 41 receives the print job data from a personal computer or the like. The print job data includes data of an image to be printed on a sheet or the like. The print rate calculation section 42 calculates the print rate by analyzing the print job data received by the print job data receiving section 41. The print rate indicates the proportion of the image on a sheet, to the area of the sheet. The power supply control section 43 adjusts the voltage that the high voltage power supply 34 applies to the ionization needles 31 according to the print rate calculated by the print rate calculation section 42.

A high print rate indicates a great amount of toner being fixed on one sheet. Thus, it can be assumed that the amount of the chemical emission being generated per sheet is also great. The power supply control section 43 increases the voltage being applied to the ionization needles 31 when the print rate is high, and reduces the voltage being applied to the ionization needles 31 when the print rate is low. The reduction of the voltage being applied to the ionization needles 31 as necessary, allows the life of the ionization needles 31 and other components to be extended.

The aforementioned embodiment takes an electrophotographic color multifunction apparatus as an example of an electronic apparatus in which the ion generator 20 is to be installed. However, the technology is not limited to this. The electronic apparatus in which the ion generator 20 is to be installed can be any electronic apparatus which generates the chemical emission, and may be for example a personal computer which generates the chemical emission from the substrates therein when used, an image forming apparatus of an inkjet method which generates the chemical emission from an ink, or the like. The electronic apparatus also includes other electrophotographic image forming apparatus such as a monochrome copier.

Second Embodiment

The second embodiment is explained below with reference to FIGS. 10 through 12. The First Embodiment is arranged such that a filter which removes dust is provided on an exhaust duct, and the ion generator is provided downstream of the filter. The present embodiment does not provide a filter which removes dust in the exhaust duct. The structure of the present embodiment is the same as the structure of the First Embodiment, except for the shape of the exhaust duct and the members arranged therein. The explanation of the components with the same structure as the First Embodiment is omitted in the present embodiment.

Figure 10:
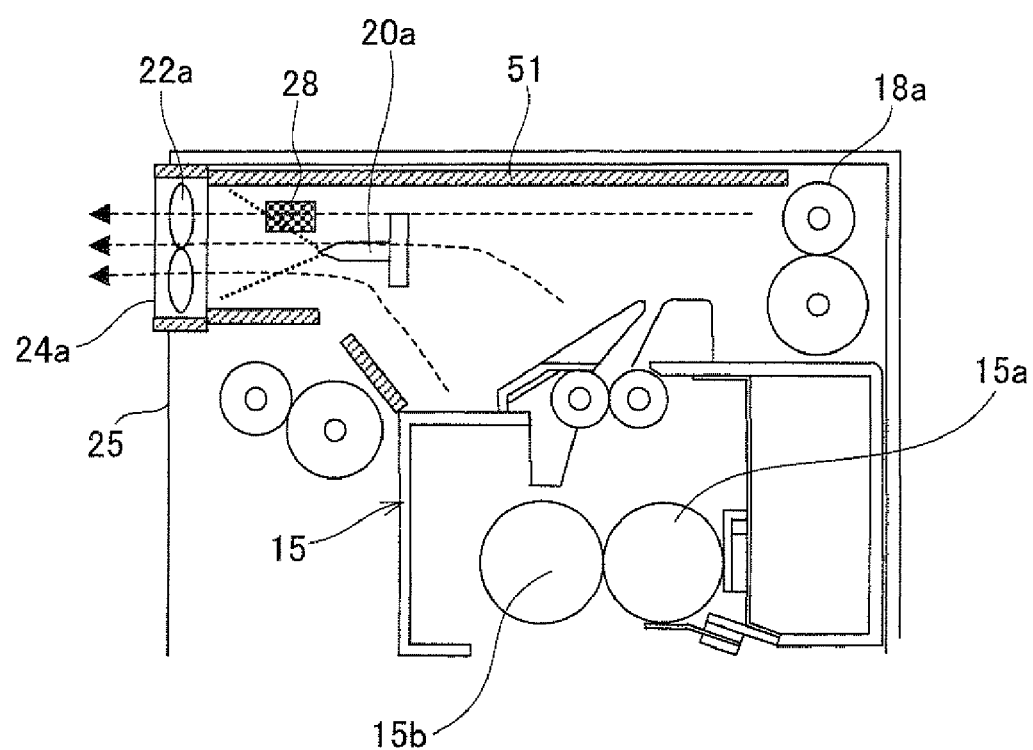
FIG. 10 illustrates a Second Embodiment and is a longitudinal sectional view of the structure of components around a duct.
Figure 11:
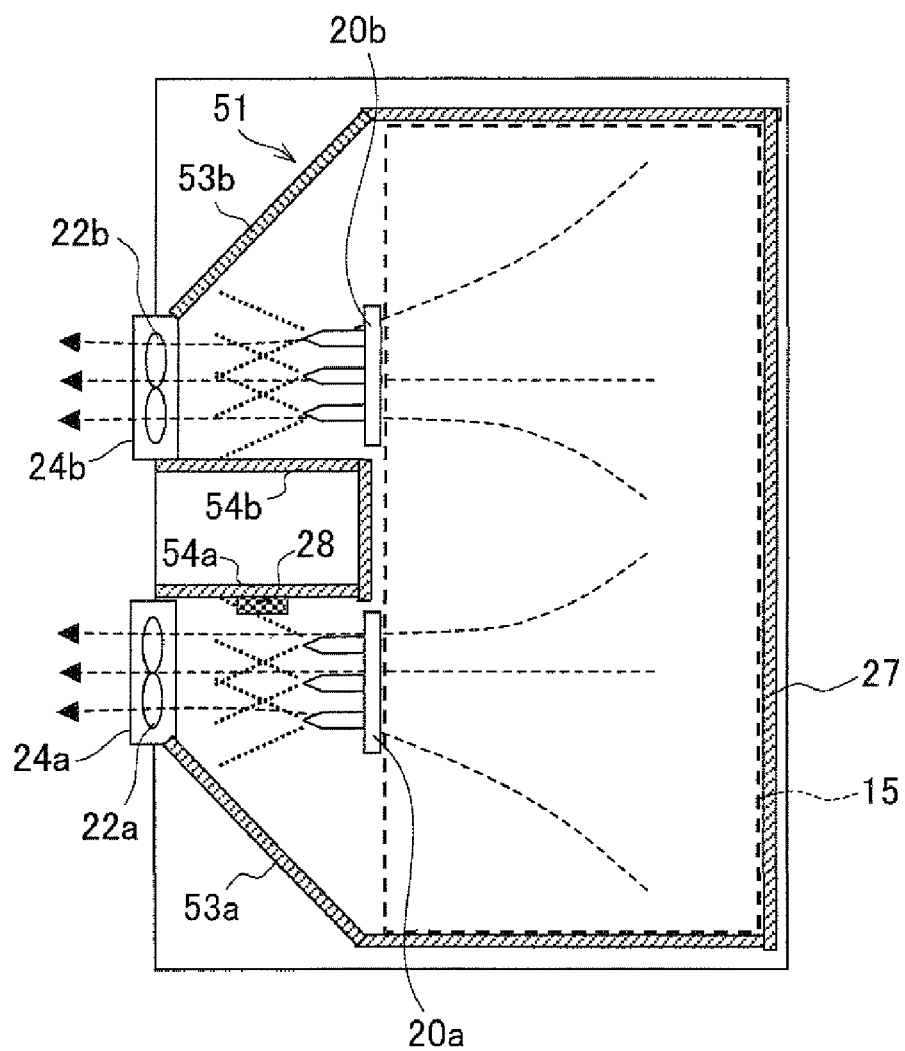
FIG. 11 illustrates a Second Embodiment and is a transverse sectional view of the structure of the components around the duct.

FIG. 10 is a longitudinal sectional view illustrating a detailed structure of the components around the duct of the present embodiment. FIG. 11 is a transverse sectional view of the duct. As illustrated in FIG. 11, a duct 51 includes a main section 27 in the same shape as the First Embodiment, the exhaust openings 24a and 24b, and two guide sections 53a and 53b. The guide sections 53a and 53b communicate with the main section 27 and the exhaust openings 24a and 24b. The guide sections 53a and 53b leads the air inside the main section 27 to the exhaust openings 24a and 24b. The passage inside the guide sections 53a and 53b narrow towards the exhaust openings 24a and 24b, being the widest at its part in contact with the main section 27.

Exhaust fans 22a and 22b are provided in the vicinity of the ends on the exhaust openings 24a and 24b side within the guide sections 53a and 53b, and the air inside the guide sections 53a and 53b is carried from the main section 27 side to the exhaust opening 24a or 24b side by the exhaust fans 22a and 22b. Therefore, as in the case with the First Embodiment, the air heated by the fixing unit 15 is collected in the main section 27 of the duct 51, and is discharged outside the housing 25 from the exhaust openings 24a and 24b passing through the guide sections 53a and 53b.

The ion generators 20a and 20b which generate the negative ion are provided inside the guide sections 53a and 53b, respectively. Each of the ion generators 20a and 20b is the same as the ion generator in the First Embodiment, and is arranged in a position in the upstream of the exhaust fans 22a and 22b in the air carrying direction. The ion generator 20a or 20b is arranged such that the needlepoint of the ionization needles 31 on the base frame 32 faces the exhaust fans 22a and 22b.

With this arrangement, the paper powder being generated in the image forming process and the toner are blocked by the base frame 32, which makes it unlikely for the paper powder and the toner to adhere on the ionization needles 31. As such, the amount of ions generated is stably maintained for a long term, even without the filter.

An experiment conducted to study the validity of the technology is explained below.

Experiment 4

An aging test was conducted to study if a difference occurred in the amount of ions being generated. The apparatuses used for the test were (i) a color multifunction apparatus with the needlepoint of the ionization needles 31 facing the direction of the exhaust fan 22a or 22b (downstream of the air carrying direction) (Example 2) as illustrated in FIG. 11 and (ii) a color multifunction apparatus with the needlepoint of the ionization needles 31 facing the direction of the main section 27 (upstream of the air carrying direction) (Comparative Example 3).

The present experiment used the color multifunction apparatuses of Example 2 and Comparative Example 3, each printing a color document with a print rate of 20% (5% per color) in a speed of 35 sheets per minute. The amount of ions generated from the ion generator was measured at the point the number of printed sheets reached 100,000. The amount of ions generated is described by percentage, 100% being the amount of ions generated at the start of printing. The result of the experiment is as illustrated in FIG. 12.

Figure 12:
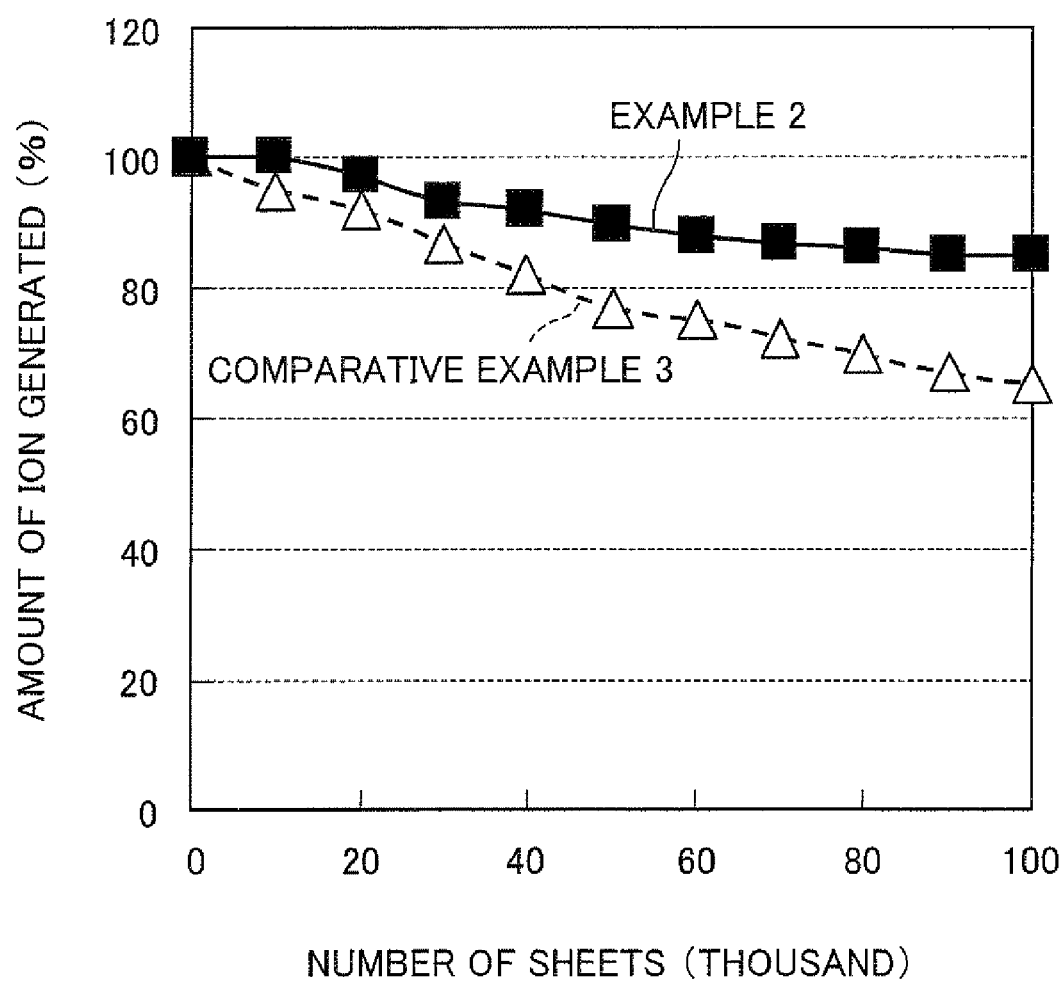
FIG. 12 illustrates the result of Experiment 4, and is a view illustrating relationship between the number of printed sheets and the amount of ions generated.

The color multifunction apparatus of the Example 2 was more capable of maintaining the amount of ions being generated, as compared to the color multifunction apparatus of the Comparative Example 3, as illustrated in FIG. 12. That is, the amount of ions being generated decreased more in the Comparative Example 3. A possible cause of this is that the base frame 32 of the ion generator 20 blocks the exhaust flow and thus prevents the ionization needles 31 from being dirty with the toner and the paper powder contained in the exhaust flow, even without a filter. Thus, it is found that the ion generator 20 is preferably arranged inside the duct 51 such that the needlepoints of the ionization needles 31 face downstream in the air carrying direction.

Third Embodiment

The third embodiment is explained below with reference to FIGS. 13 through 16. The First and Second Embodiments are arranged such that two ion generators which generate negative ions are provided in the exhaust duct. On the other hand, the present embodiment includes an ion generator which generates negative ions, and also an ion generator which generates positive ions. The color multifunction apparatus is the same in structure as that employed in the First and Second Embodiments, except for the shape of the exhaust duct and the members arranged therein. The explanation for the structures which is the same as the First and Second Embodiments is omitted in the present embodiment.

Figure 13:
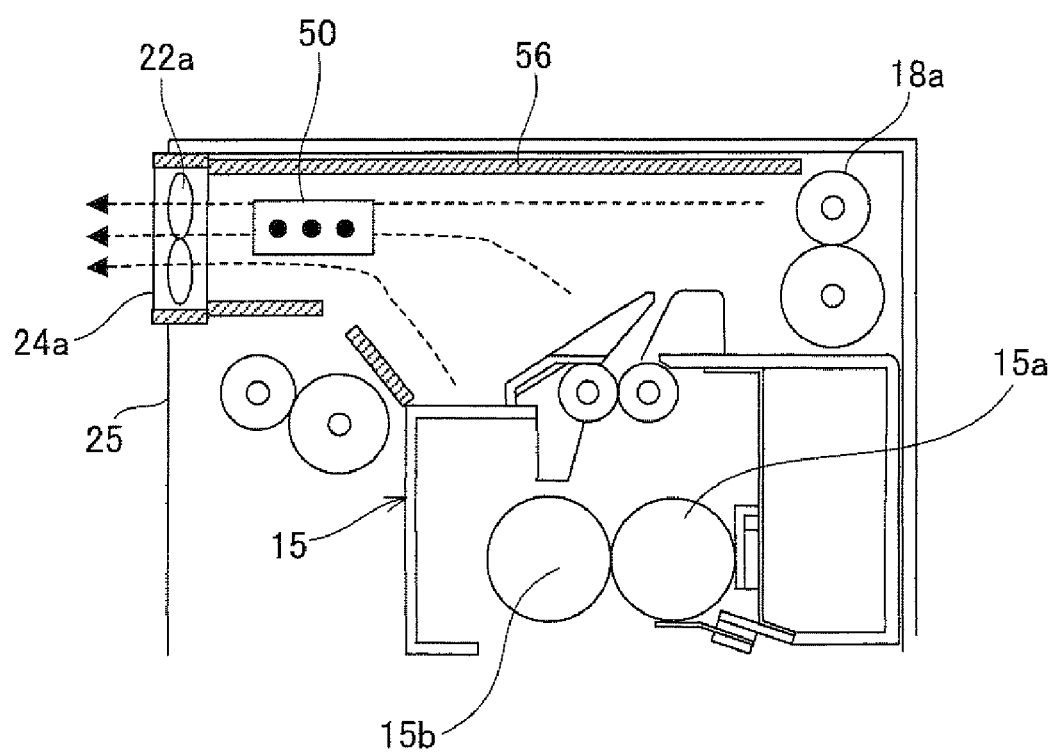
FIG. 13 illustrates a Third Embodiment and is a longitudinal sectional view illustrating the structure of components around a duct.
Figure 14:
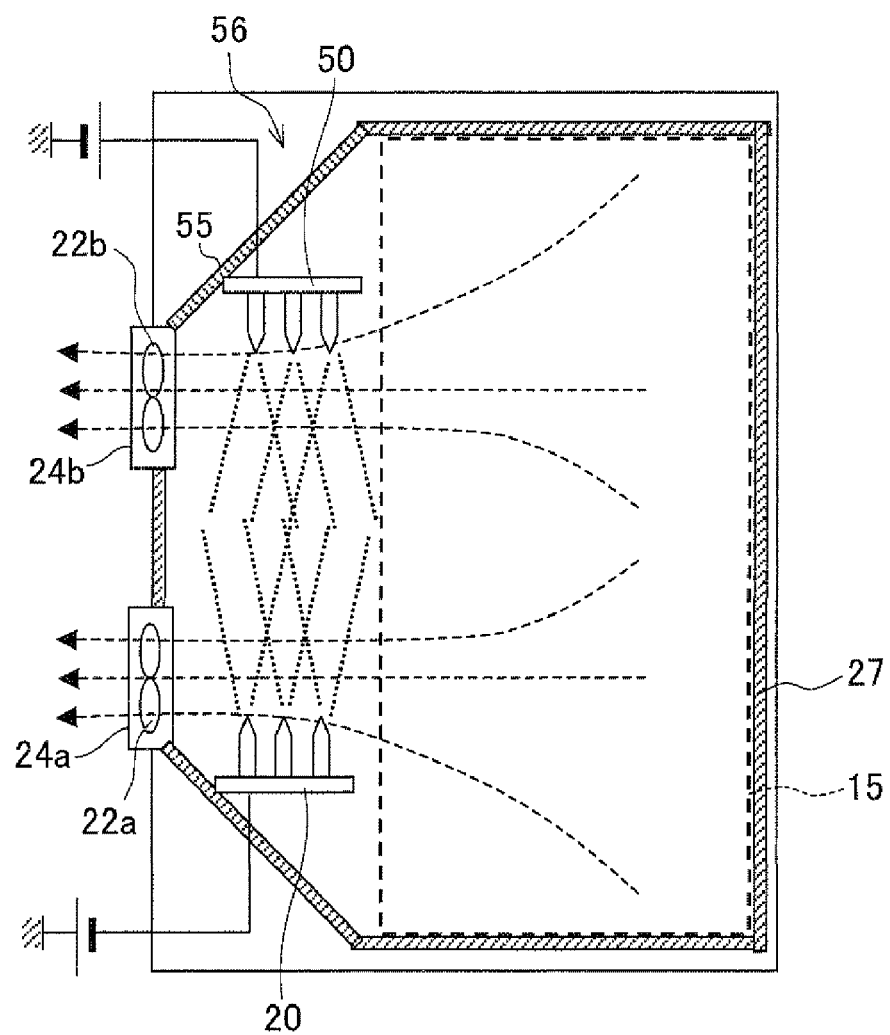
FIG. 14 illustrates a Third Embodiment and is a transverse sectional view illustrating the structure of the components around the duct.

FIG. 13 is a longitudinal sectional view illustrating the details of the components around a duct of the present embodiment, and FIG. 14 is a transverse sectional view of the duct. As illustrated in FIG. 13, the duct 56 includes a main section 27 in the same shape as the First Embodiment, exhaust openings 24a and 24b, and a single guide section 55. The guide section 55 communicates with the main section 27 and the exhaust openings 24a and 24b, and leads the air inside the main section 27 to the exhaust sections 24a and 24b. A passage to lead the air to the exhaust opening 24a and a passage to lead the air to the exhaust opening 24b are provided separately in the First and Second Embodiment; however, the passages are made common (integrated) in the present embodiment.

The passage inside the guide section 55 narrows towards the exhaust opening 24a and 24b, and is the widest in the part in contact with the main section 27. Exhaust fans 22a and 22b are arranged around the exhaust openings 24a and 24b of the guide section 55, which carries the air inside the guide section 55 from the main section 27 side to the exhaust opening 24a and 24b side. Therefore, as in the case with the First Embodiment, the air heated by the fixing unit 15 is collected in the main section 27 of the duct 51, and is discharged from the exhaust openings 24a and 24b to the outside of the housing 25 via the guide section 55.

The present embodiment is arranged such that two ion generators 20 and 50 are arranged facing each other, inside the guide section 55 in the duct 56. The ion generator 20 generates negative ions by having a voltage of −5 kV applied to the ionization needles 31, as in the case with the First and Second Embodiment. The ion generator 50 has the same structure as the ion generator 20, however the voltage applied to the ionization needles 31 is positive (+5 kV in the embodiment), which generates positive ions in the atmosphere. For convenience, the members in the ion generator 50 are given the same reference numerals as those of the ion generator 20.

The ion generator 20 and the ion generator 50 are arranged such that the ionization needles 31 thereof face each other, and both air flow passages flowing to the exhaust opening 24a and the exhaust opening 24b are sandwiched between the ionization needles 31 of the ion generators 20 and 50. This structure allows the air flowing through the two passages to be exposed to both the positive and negative ions.

Many of the volatile chemical compounds such as the odor and the VOC are positively charged; however, some of them are negatively charged. Whichever polarity the volatile chemical compound is charged in, it is possible to effectively reduce the amount of volatile chemical compound by generating both positive and negative ions as in the present embodiment.

There is also the effect that the interaction with the two ion generators 20 and 50 having the opposite polarities increases the distance to which the generated ions travel. If there is only one ion generator, the ions generated in the vicinity of the ion generator randomly diffuse in various directions by the repulsive force between the substances having the same polarity. On the contrary, in the present embodiment, the ion generator 50 which generates the positive ions is provided at a position facing the ion generator 20 which generates the negative ions. This generates attractive forces between the negative ions being generated by the ion generator 20, the positive ions being generated in the vicinity of the ion generator 50, and the electrode of the ion generator 50. Thus, the negative ions being generated by the ion generator 20 is induced to the ion generator 50 which is arranged facing the ion generator 20.

As such, the distance to which the generated ions travel increases. The inactivation of the chemical emission is thus effectively performed by providing the flow passage for the air containing the chemical emission between the two ion generators, in which the volatile chemical substance is exposed to both the positive and negative ions of a high concentration.

In the present embodiment, the ion generators 20 and 50 are arranged inside the duct 56 for fixing. However, the effect of the present embodiment can be sufficiently obtained even if the ion generators 20 and 50 are provided outside the housing 25. This is because the reach of the ions is broadened as compared to the case where only the conventional negative ion generator is provided.

Described below is an experiment conducted in order to study the validity of the technology.

Experiment 5

The present experiment studied if the distance to which the ions travel is increased by the arrangement in which the ion generator 20 which generates the negative ions and the ion generator 50 which generates the positive ions are provided in a position facing each other.

Figure 15:
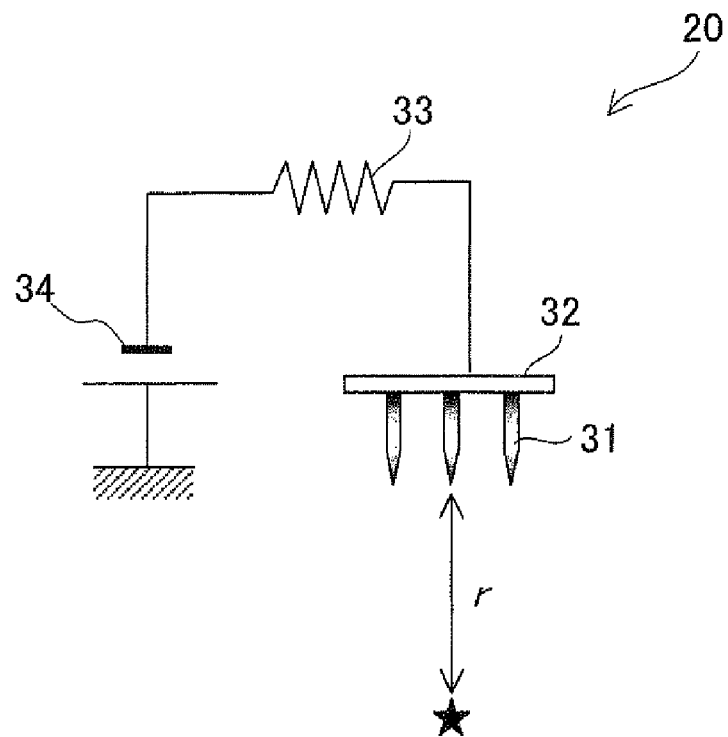
FIG. 15 is a view illustrating the arrangement of the members in Experiment 5.
Figure 15:
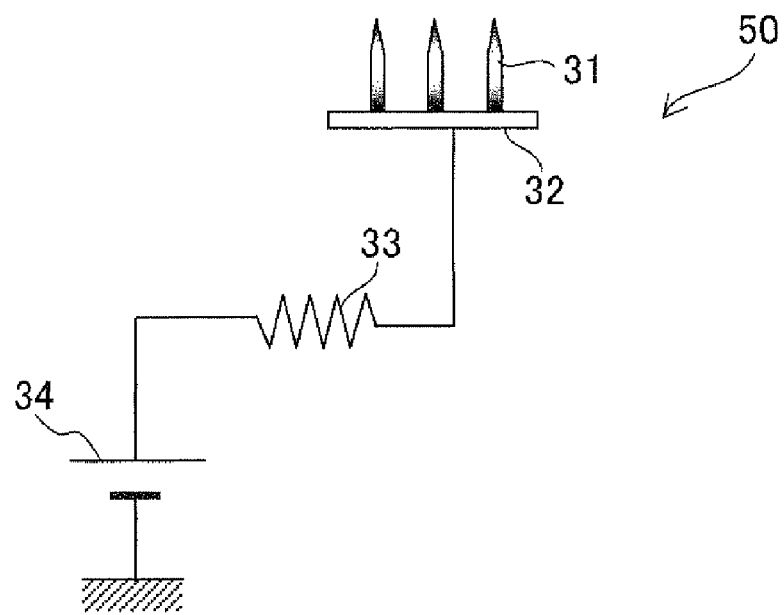
Figure 16:
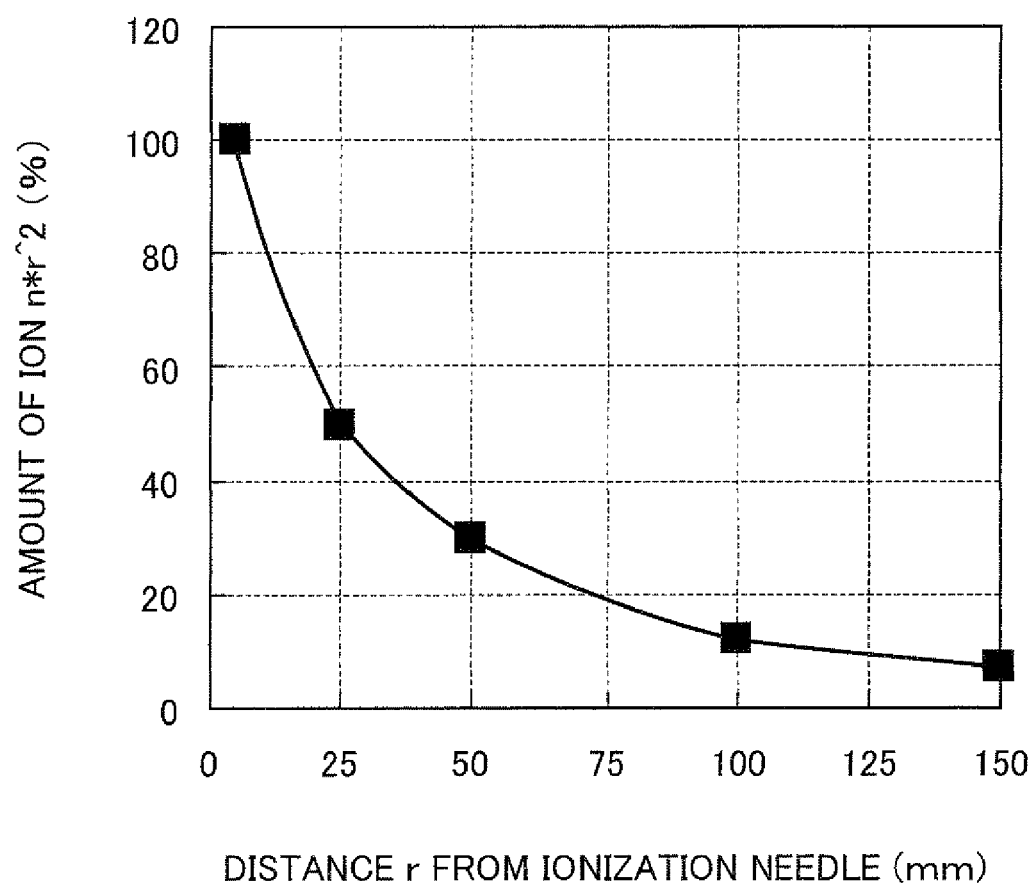
FIG. 16 illustrates the result of Experiment 5, and is a view illustrating relationship between a distance from a needle-point of the ionization needle of the ion generator and the amount of ions.

FIG. 15 is a view illustrating the arrangement of the ion generators 20 and 50 in the present experiment. The concentration of the negative ions in the atmosphere was measured, with varying distances from the ionization needles 31 as in Experiment 1. The voltages of −5 kV and +5 kV were applied to the base frames 32 of the ion generator 20 and the ion generator 50, respectively. The device used for the measurement was the same as that in Experiment 1. The result of the experiment is as illustrated in FIG. 16. The "distance r" in FIG. 16 is a distance from the central ionization needle 31, as illustrated in FIG. 15.

It is found that, when compared with the result of Experiment 1 (FIG. 5), the distance to which the negative ions being generated by the ion generator 20 travel increases with the arrangement in which the ion generator 50 which generates the positive ions faces the ion generator 20 which generates the negative ions.

As in this experiment, if there is a certain space provided between the ion generator 20 which generates the negative ions and the ion generator 50 which generates the positive ions when arranging the two generators, the reaction of the positive and negative ions canceling out their effects has hardly any impact on the reaction.

Fourth Embodiment

The fourth embodiment is described below with reference to FIGS. 17 through 20. The First to Third Embodiments use the electronic discharge type ion generator as illustrated in FIG. 4. On the other hand, the present embodiment uses a surface discharge type ion generator. The present embodiment has the same structure as the Third Embodiment, except for the ion generator and the arrangement thereof inside the duct. The explanation of the members having the same structures as the First to Third Embodiment is omitted in the present embodiment.

Figure 17:
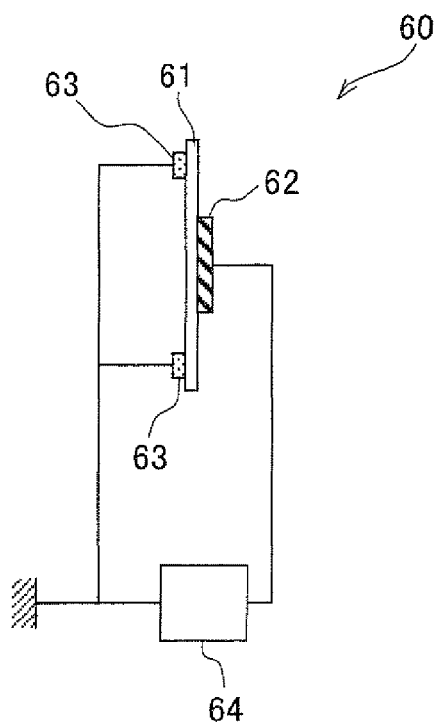
FIG. 17 illustrates one embodiment and is a side view illustrating a surface discharge type ion generator.
Figure 18:
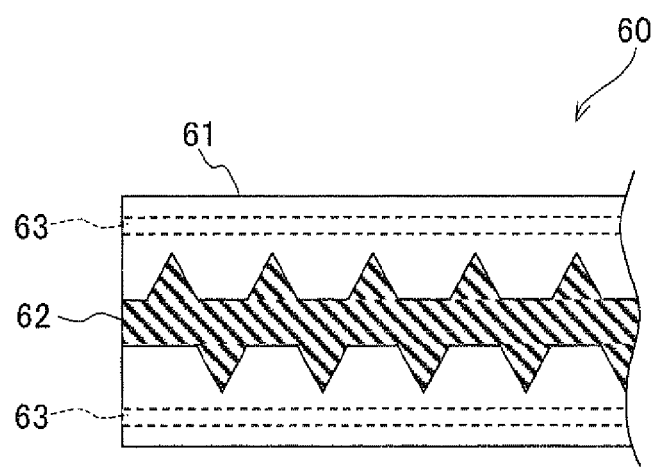
FIG. 18 is a plan view illustrating an electrode section of the ion generator illustrated in FIG. 17.

FIG. 17 is a side view illustrating an ion generator being used in the color multifunction apparatus in the present embodiment. FIG. 18 is a plan view illustrating the electrode section of the ion generator. The ion generator 60 is of a type generating the ion by utilizing a surface discharge, and the electrode section is of a three-layered structure. Specifically, one planar discharge electrode (first planar electrode) 62 made from stainless steel, tungsten or the like is arranged on the front side of the plate-shaped dielectric (insulator member) 61 made from ceramic, mica or the like, and two planar induction electrodes (second planar electrode) 63 also made from stainless steel, tungsten or the like is arranged on the back side of the plate-shaped dielectric 61. Both the discharge electrode 62 and induction electrodes 63 are fabricated on the dielectric 61 by an etching process.

The dielectric 61 is of a rectangular plate shape. On the other hand, the discharge electrode 62 is of a serrate shape, and the induction electrodes 63 are of a line shape, in which each are arranged extending along the longitudinal direction of the dielectric 61. The discharge electrode 62 is arranged in the center in the lateral direction of the dielectric 61. The two induction electrodes 63 are arranged on the upper side and the lower side of the center in the lateral direction of the dielectric 61, respectively. The shapes of the discharge electrode 62 and the induction electrodes 63 are not limited as the aforementioned, and for example the discharge electrode 62 may be of a line shape.

A predetermined driving voltage of a pulse shape (a frequency of 1.5 kHz, a voltage in a range of 0 to −3 kV, a duty of 10% in the embodiment) is applied between the discharge electrode 62 and the induction electrodes 63 by the high voltage power supply 64. The induction electrodes 63 are grounded, and application of the voltage by the high voltage power supply 64 makes the discharge electrode 62 hold a potential in a range of 0 to −3 kV towards the induction electrodes 63. With this, the surface discharge is generated between the discharge electrode 62 and the induction electrodes 63, which ionizes the air between the discharge electrode 62 and the induction electrodes 63 and thus generate the negative ions.

Figure 19:
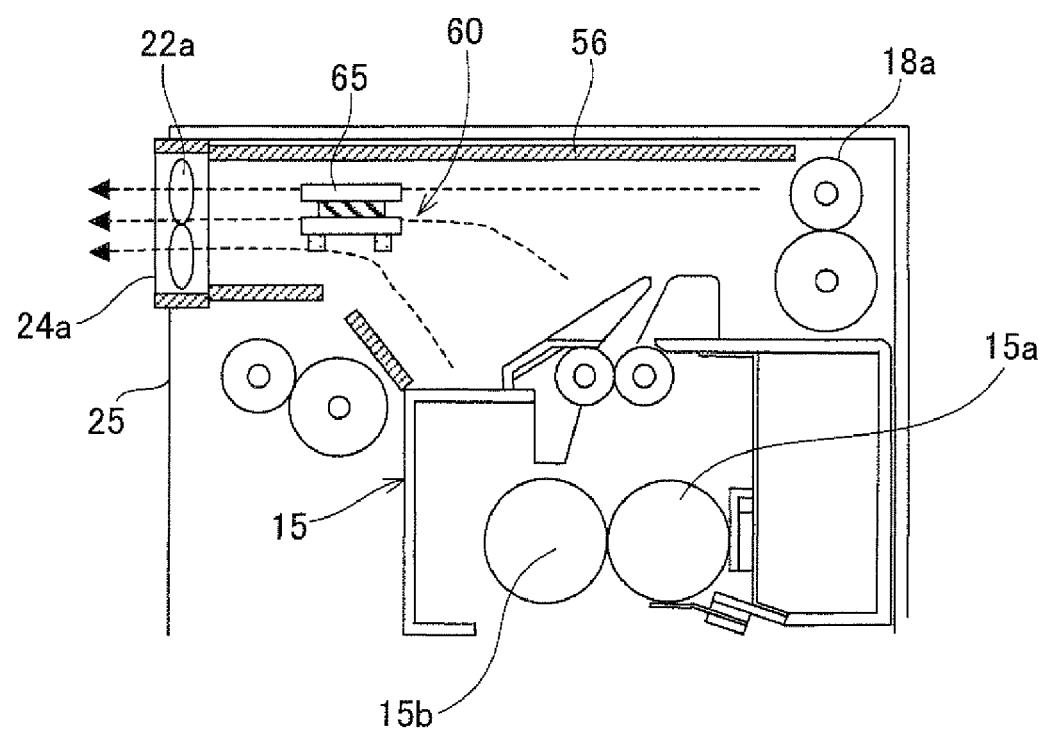
FIG. 19 illustrates a Fourth Embodiment and is a longitudinal sectional view illustrating the structure of components around a duct.
Figure 20:
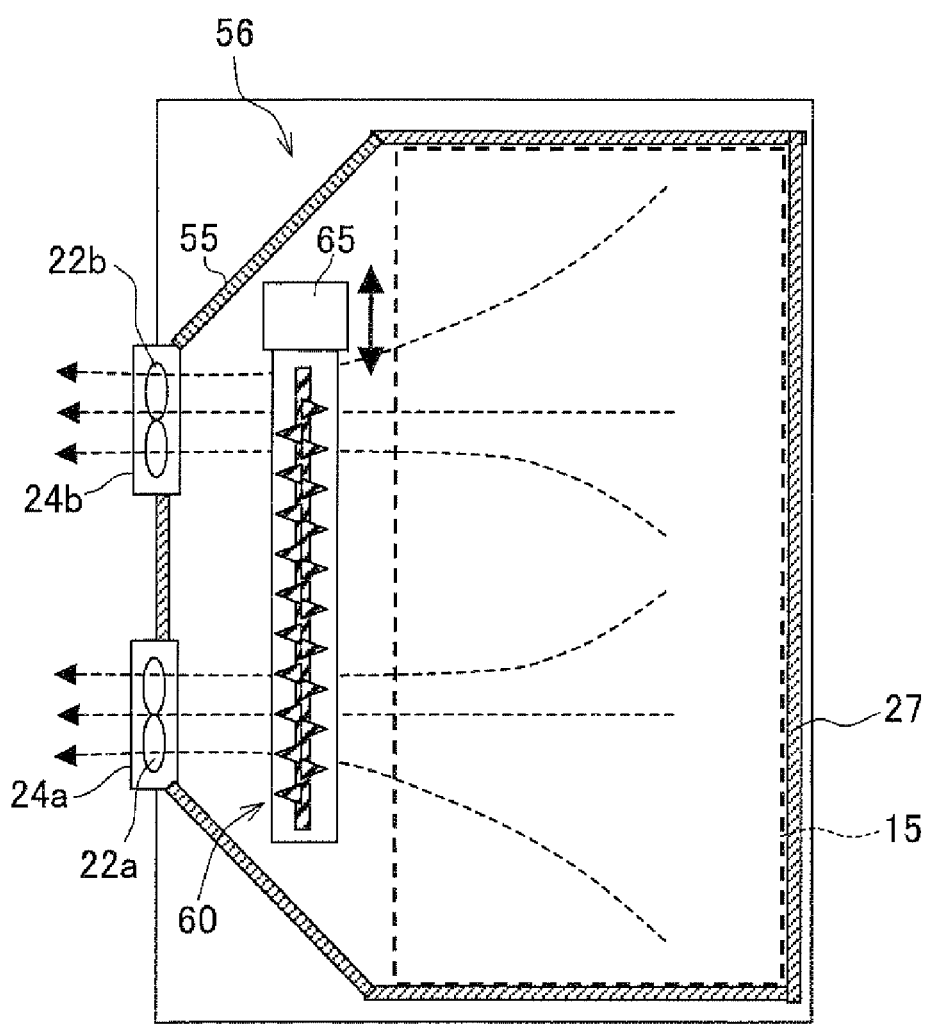
FIG. 20 illustrates a Fourth Embodiment and is a transverse sectional view illustrating the structure of the components around the duct.

FIG. 19 is a longitudinal sectional view illustrating the detailed structure of the components around the duct of the present embodiment. FIG. 20 is a transverse sectional view of the duct. The ion generator 60 is arranged inside the guide section 55 of the duct 56 and on the flow passages to the exhaust openings 24*a* and 24*b* such that the longitudinal direction of the dielectric 61 traverses both the flow passages to the exhaust openings 24*a* and 24*b*, as illustrated in FIGS. 19 and 20. The ion generator 60 is also arranged in such a position that the discharge electrode 62 faces upwards, the induction electrode 63 faces downwards, and the plate-shaped dielectric 61 is horizontal.

The negative ions generate when the voltage is applied between the discharge electrode 62 and induction electrodes 63 of the ion generator 60, and are diffused in the upward direction of the ion generator 60. Thus, the volatile chemical compound which flows inside the two flow passages is exposed to the negative ions.

Furthermore, the present embodiment includes a cleaning member 65 which cleans the surface of the discharge electrode 62 of the ion generator 60, as illustrated in FIGS. 19 and 20. The cleaning member 65 is in contact with the upper side of the planar discharge electrode 62, and is provided slidable in the direction of the arrow in FIG. 20 (the longitudinal direction of the dielectric 61). The upper surface of the discharge electrode 62 is wiped with the cleaning member 65 when the cleaning member 65 is slid, removing the toner, paper powder, corona products and the like adhered to the discharge electrode 62. The cleaning member 65 may be formed by for example felt, and is slid by a manual or an arbitrary driving mechanism.

The ion generator 60 of the surface discharge type has a shorter traveling distance (approximately 5 mm), as compared to the ion generator 20 of the needle-shaped type (electronic discharge type). However, it is less likely for the corona product to adhere on the electrode since a planar electrode is used, and even if the corona product does adhere, it can be easily cleaned. Thus, the ions can be stably generated for a long term.

Fifth Embodiment

The fifth embodiment is described below with reference to FIG. 21. In the Third Embodiment, two ion generators are provided generating ions having the negative polarity and ions having the positive polarity, respectively. On the other hand, in the present embodiment, one ion generator generates ions of both polarities. The structure of the present embodiment is the same as the First Embodiment, except for the structure of the ion generator, and the explanation of the structures that are the same as the First Embodiment is omitted in the present embodiment.

Figure 21:
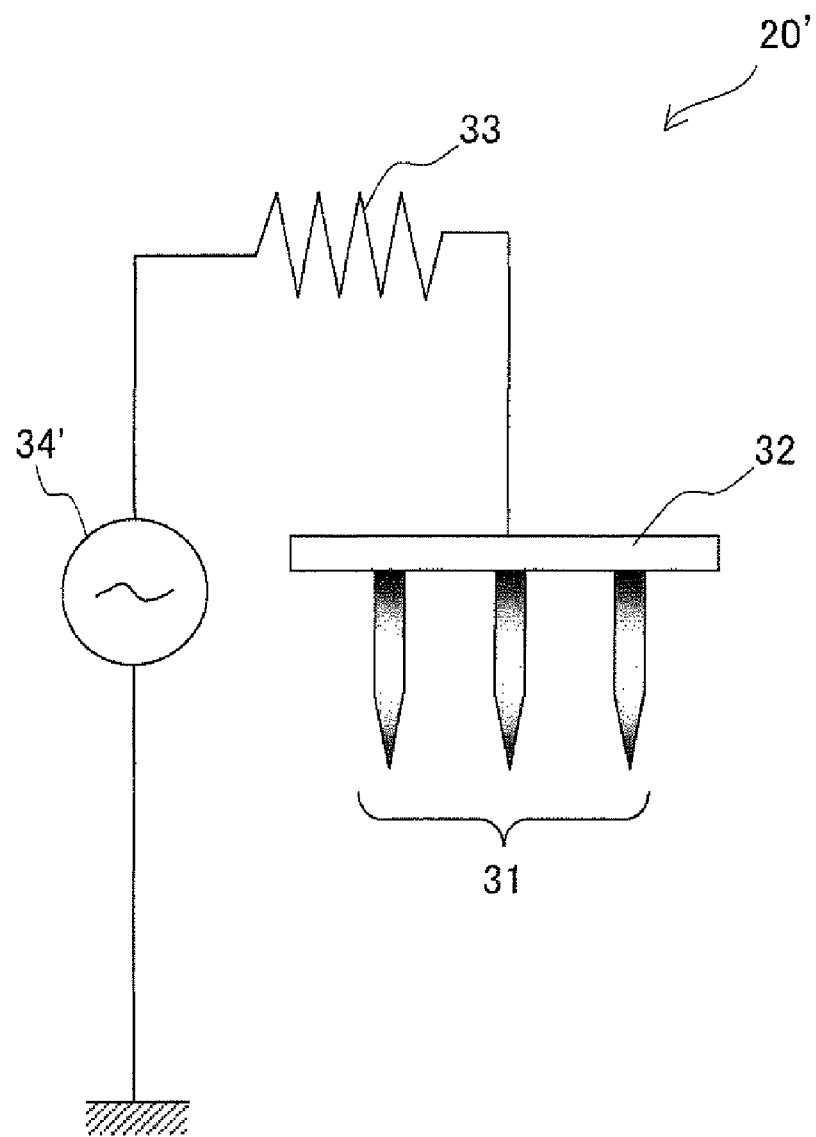
FIG. 21 illustrates a Fifth Embodiment and is a side view illustrating an ion generator applying an alternating voltage to an ionization needle.

FIG. 21 is a side view illustrating the ion generator 20' of the present embodiment. The ion generator 20' includes a plurality (three in the embodiment) of ionization needles 31, a base frame 32 to support the ionization needles 31, a high voltage power supply 34' to make voltage of the ionization needles 31 higher than that of a ground, and a fixed resistor 33, as in the First Embodiment. The connection configuration of each member and the structures of the ionization needles 31 the base frame 32 and the fixed resistor 33 are the same as the First Embodiment.

The high voltage power supply 34' is a power supply which applies an alternating voltage (for example a voltage in a range of +4.0 to −4.0 kV, in a frequency of 1 kHz). One electrode of the high voltage power supply 34' is connected to the base frame 32 via the fixed resistor 33, and the other electrode thereof is grounded. The ionization needles 31 will alternately have a high positive potential and a high negative potential with respect to the ground, by being applied the alternating voltage from the high voltage power supply 34'. This alternately generates the negative ion and positive ion into the atmosphere in the vicinity of the ionization needles 31.

The ion generator 20' of the present embodiment can thus effectively reduce the amount of the chemical emission contained in the atmosphere, regardless of the polarity in which the chemical emission is charged. It is also possible to attain downsizing and cost reduction of the multifunction apparatus 100 as compared to the Third Embodiment, since the one ion generator 20' can generate both the negative ion and the positive ion.

However, the distance to which the negative ions travel shortens if the ion generator 20' is used. Therefore, the combination of the ion generator 20 and the ion generator 50 as in the Third Embodiment is preferably used to increase the distance to which the negative ions travel.

Sixth Embodiment

The sixth embodiment is described below with reference to FIGS. 22 through 26. The present embodiment is arranged such that the ions are effectively reacted with the chemical emission by providing a counter electrode facing the ionization needle. The structure of the present embodiment is the same as that of the First Embodiment except for the structure of the ion generator, and the explanations of the same structures as the First Embodiment is omitted in the present embodiment.

Figure 22:
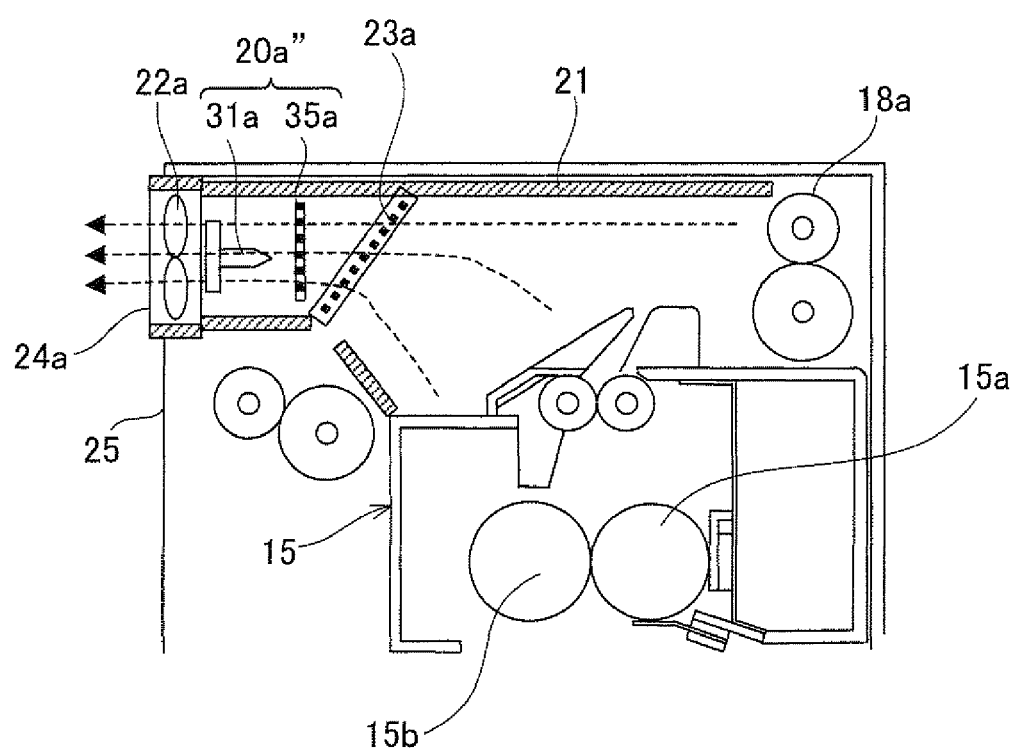
FIG. 22 illustrates a Sixth Embodiment and is a longitudinal sectional view illustrating the structure of components around a duct.

FIG. 22 is a view illustrating detailed structures of the components around the duct 21 of the present embodiment. The present embodiment provides a counter electrode 35*a* facing the ionization needle 31*a* of the ion generator 20*a*", as illustrated in FIG. 22. The counter electrode 35*a* is arranged between the ionization needle 31*a* and a filter 23*a*.

This structure is the same for another ion generator 20*b*", corresponding to the ion generator 20*b* of the First Embodiment. Thus, in the following explanation, the ion generator 20*a*" and 20b" are referred collectively to as an ion generator 20".

Figure 23:
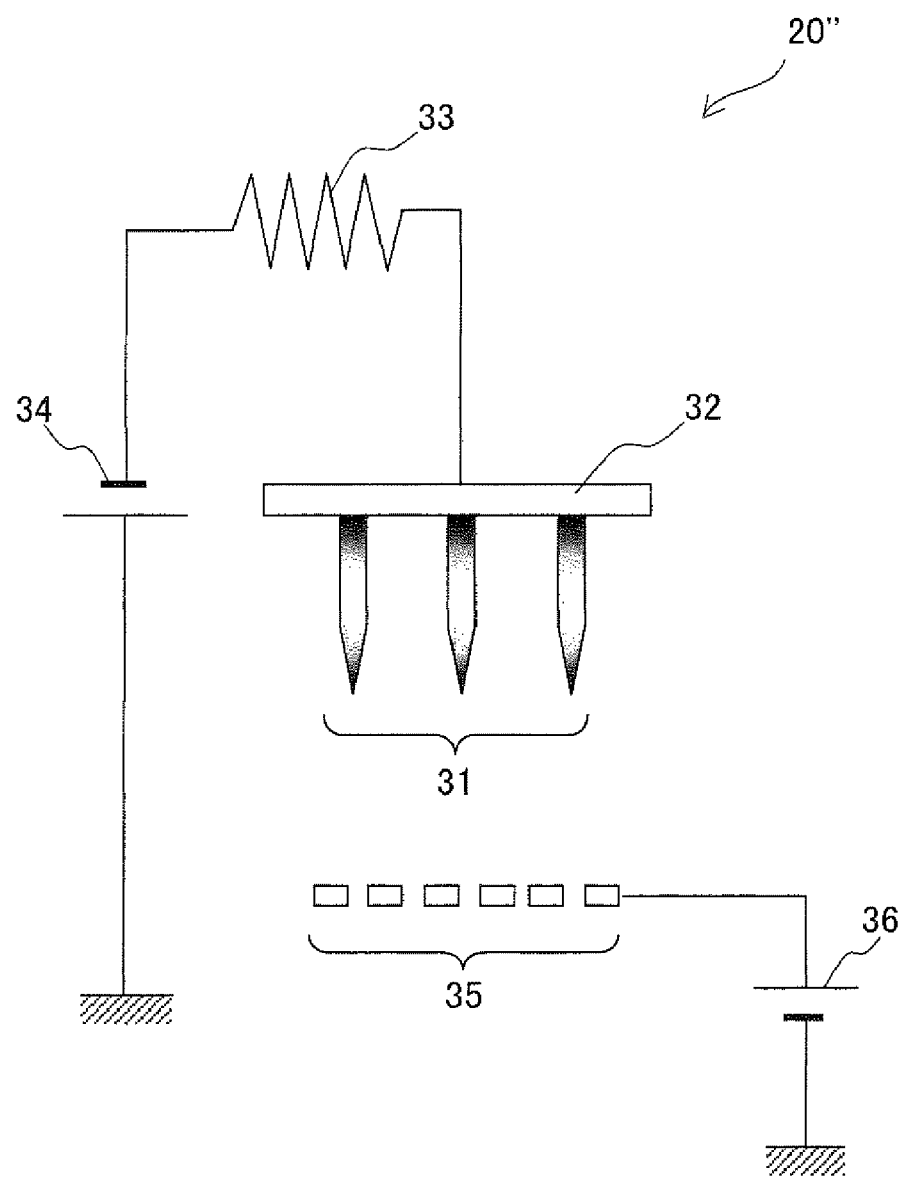
FIG. 23 illustrates a Sixth Embodiment and is a side view illustrating an electronic discharge type ion generator having a counter electrode.

FIG. 23 is a side view illustrating the ion generator 20" of the present embodiment. The ion generator 20" includes a plurality (three in the embodiment) of ionization needles 31, the base frame 32 to support the ionization needles 31, a high voltage power supply 34' to make voltage of the ionization needles 31 higher than that of a ground, and a fixed resistor 33, as in the First Embodiment, as illustrated in FIG. 23. The connection configuration and the structures of the members are the same as the First Embodiment.

The ion generator 20" further includes a counter electrode 35 arranged facing the ionization needles 31 and a power supply 36 which applies the voltage to the counter electrode 35. Specifically, the counter electrode 35 is a lattice-shaped electrode, and the lattice plane is provided facing the needle-points of the ionization needles 31. As the counter electrode, for example a SUS (Stainless used steel) may be used. The power supply 36 has the positive electrode connected to the counter electrode 35, and the negative electrode grounded.

The counter electrode 35 holds a positive potential towards the ground when a positive voltage is applied by the power supply 36. As a result, the negative ion being generated in the atmosphere in the vicinity of the ionization needles 31 is strongly attracted towards the direction of the counter electrode 35 having the positive potential, creating a strong negative ion flow. Thus, it is possible to react the negative ions of a high concentration with the chemical emission and efficiently remove the chemical emission.

(Modification)

Figure 24:
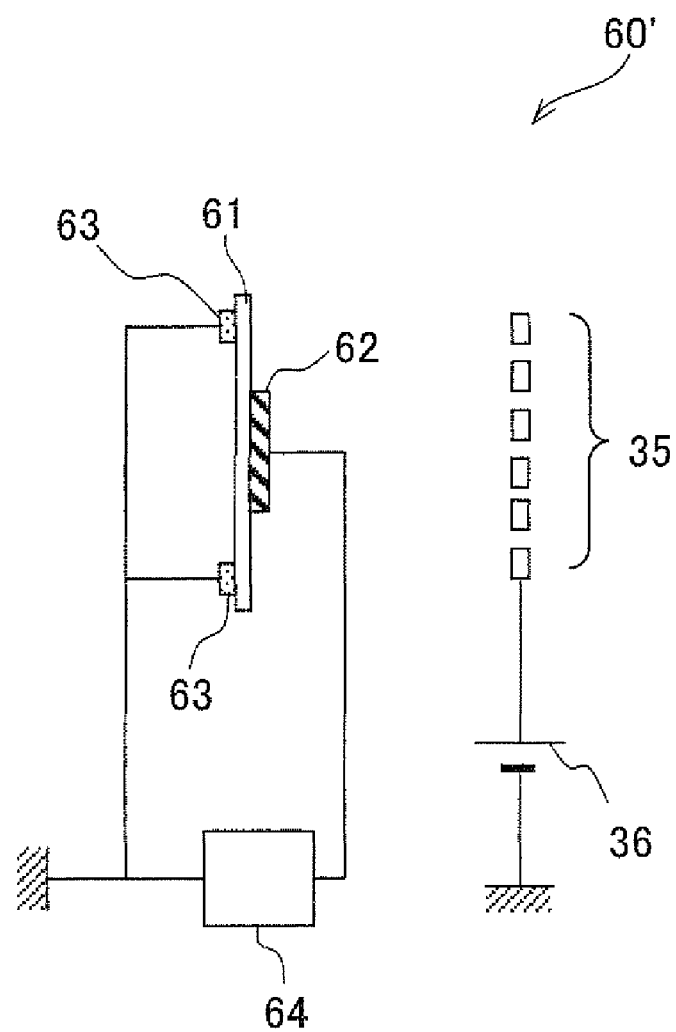
FIG. 24 illustrates a modification of Fourth and Sixth Embodiments, and is a side view illustrating a surface discharge type ion generator having a counter electrode.

The structure using the counter electrode is not limited to the structure illustrated in FIG. 23. FIG. 24 illustrates modification of the Fourth and Sixth Embodiment, and is a side view illustrating the ion generator 60' of a surface discharge type using a counter electrode. The explanation of the members having the same structures as those of the Fourth and Sixth Embodiments is omitted in the present modification.

As illustrated in FIG. 24, the ion generator 60' is the one which generates the ions using the surface discharge, and includes an dielectric 61, a discharge electrode 62 and induction electrodes 63, which serve as an electrode section, and a high voltage power supply 64 which applies pulse-shaped driving voltage between the surface electrode 62 and the induction electrodes 63. These members have the same structure as those in the Fourth Embodiment.

The ion generator 60' further includes a counter electrode 35 which is arranged facing the planar discharge electrode 62, and a power supply 36 for applying a voltage to the counter electrode 35. The counter electrode 35 in the present modification is a lattice-shaped electrode as in the Sixth Embodiment, and is arranged such that the lattice plane faces the surface of the discharge electrode 62 (the opposite side of the surface that has contact with the dielectric 61). The power supply 36 has the positive electrode connected to the counter electrode 35 and the negative electrode grounded.

As in Sixth Embodiment, the counter electrode 35 holds positive potential with respect to the ground when a positive potential is applied thereto by the power supply 36, also in the present modification. This causes the negative ion generated between the discharge electrode 62 and the induction electrodes 63 to be attracted strongly towards the direction of the counter electrode 35 which holds the positive potential, thus generating a strong negative ion flow. As a result of this, it is possible to react negative ions of a high concentration with the chemical emission and thus effectively remove the chemical emission, as in the aforementioned embodiments.

Described below is an explanation of an experiment conducted to study the validity of the technology.

Experiment 6

The present experiment studied the effect of the ion generator 20" with the structure described in Sixth Embodiment, by conducting the same experiment as Experiment 3. Specifically, by using the color multifunction apparatus MX-4500N manufactured by Sharp Corporation equipped with the ion generator 20" inside the duct within the housing (however the filter 23 is not arranged) (Example 3) as illustrated in FIG. 22, the increase values of the odor and TVOC value were measured under the same conditions as the Experiment 3.

The counter electrode 35 is a stainless steel SUS316, and was arranged in such a manner that the distance from the needlepoint of the central ionization needle 31 of the three ionization needles 31 is 30 mm. A voltage of −10 kV was applied to the ionization needles 31 of the ion generator 20", and a voltage of +1.5 kV was applied to the counter electrode 35. The result of the experiment is illustrated in FIGS. 25 and 26, together with the result of the Experiment 3.

Figure 25:
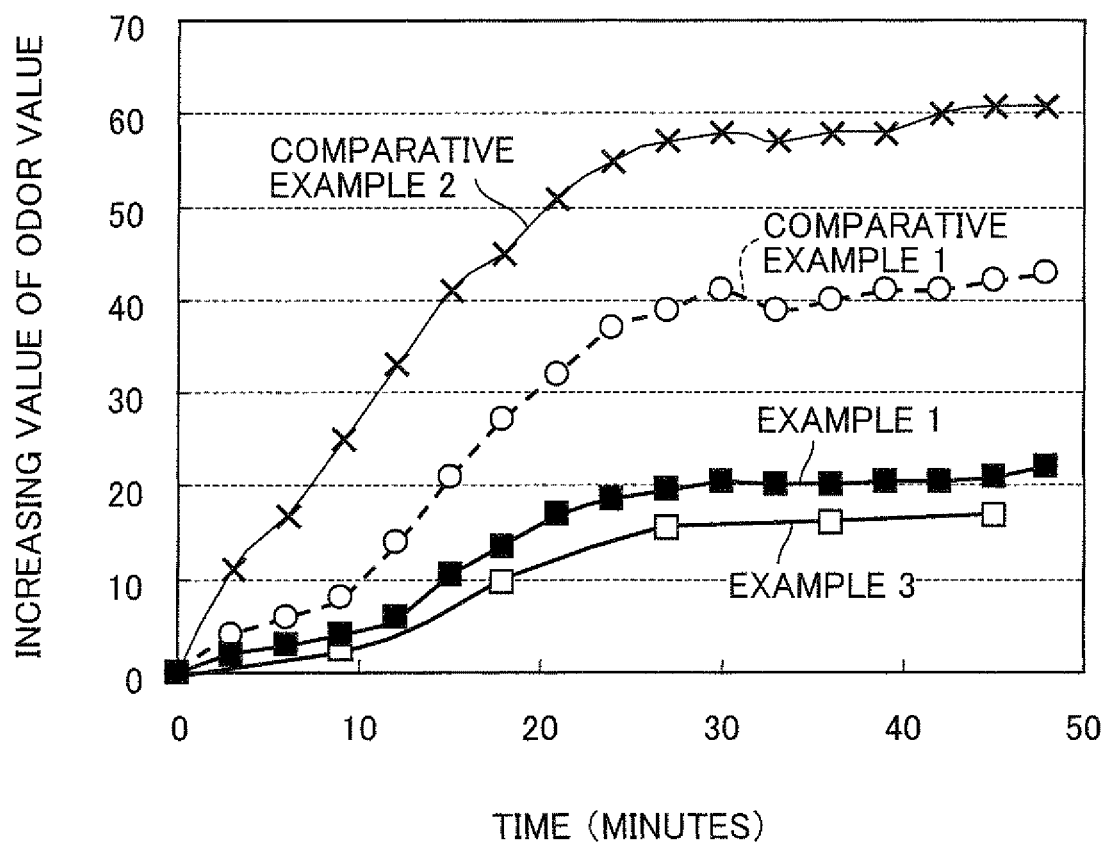
FIG. 25 illustrates the result of Experiment 6, and is a view illustrating relationship between an elapsed time and an increasing value of an odor value.
Figure 26:
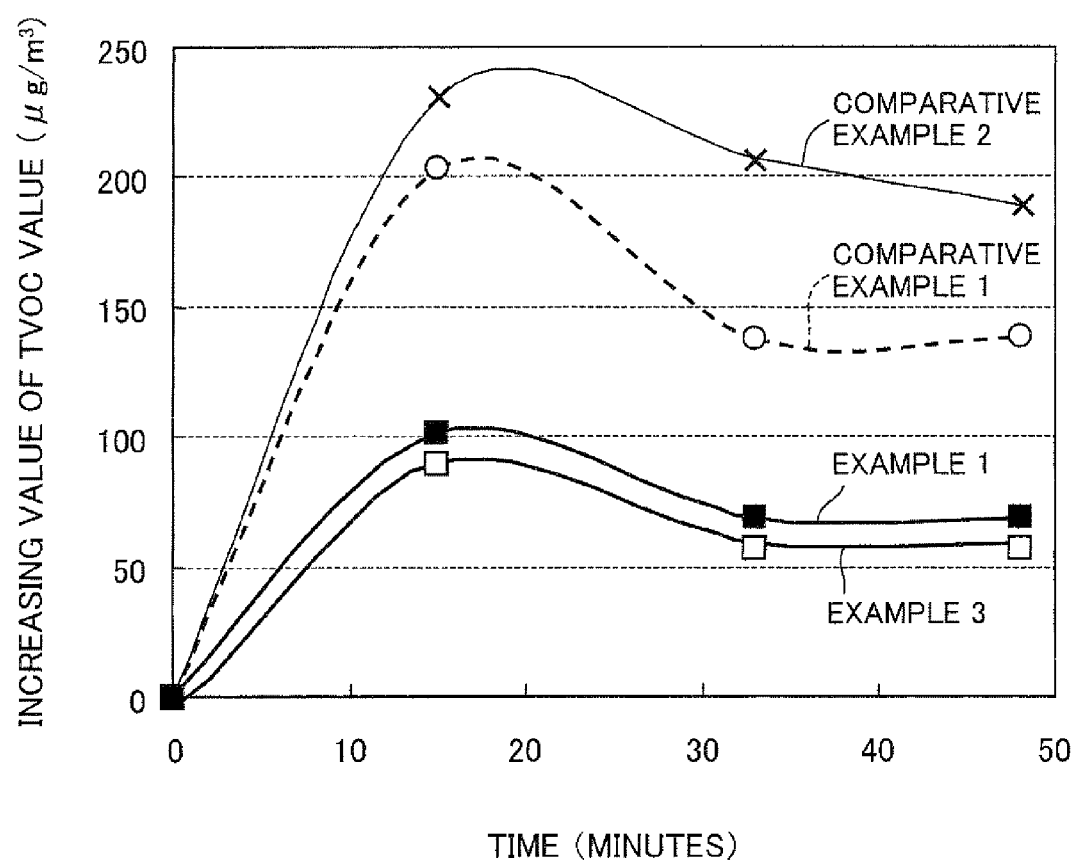
FIG. 26 illustrates the result of Experiment 6, and is a view illustrating the elapsed time and an increasing value of a TVOC value.

As illustrated in FIGS. 25 and 26, it is found that with the ion generator 20" having the counter electrode 35, the odor and the VOC are more effectively reduced as compared to the Example 1 in Experiment 3. A possible cause of this is that the odor and the VOC are effectively reduced by a strong ion flow being generated by the ion generator 20" in which the counter electrode 35 faces the ionization needles 31 and the positive voltage is applied to the counter electrode 35.

Seventh Embodiment

A seventh embodiment is explained below with reference to FIGS. 28 through 30. In the present embodiment, the ion generator is arranged so that the generated ions are emitted toward the fixing unit 15. More specifically, the ion generator is arranged inside the fixing unit 15, so that the generated ions are emitted toward the fixing nip area from which a sheet is discharged. As such, the present embodiment is arranged such that the ion further effectively reacts with the chemical emission being generated in the fixing unit 15, utilizing the high humidity environment caused by the vapor generating within the fixing unit 15.

Figure 29:
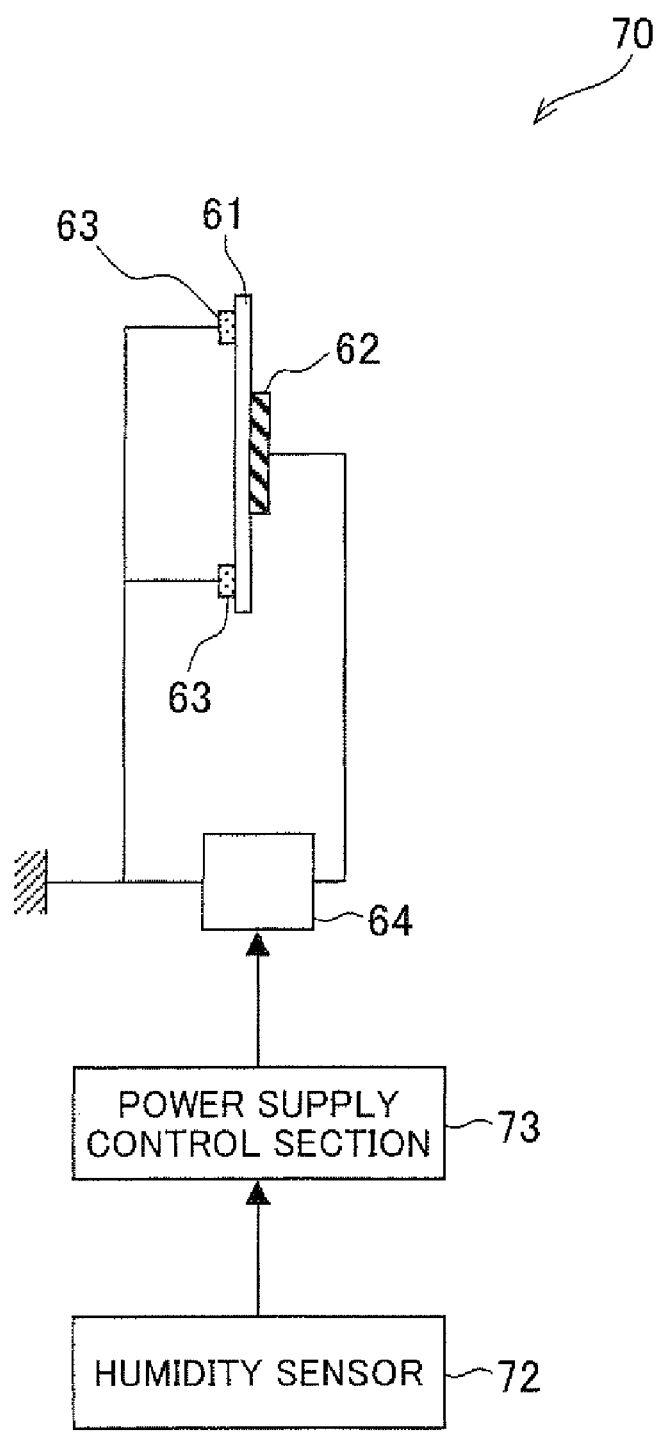
FIG. 29 illustrates a Seventh Embodiment and is a schematic view illustrating the structure of a surface discharge type ion generator.

An ion generator 70 in the present embodiment is of a type that is the same as the ion generator 60 of the surface discharge type, as illustrated in FIG. 29. For this reason, the explanation of the ion generator 70 is omitted in the present embodiment.

Figure 28:
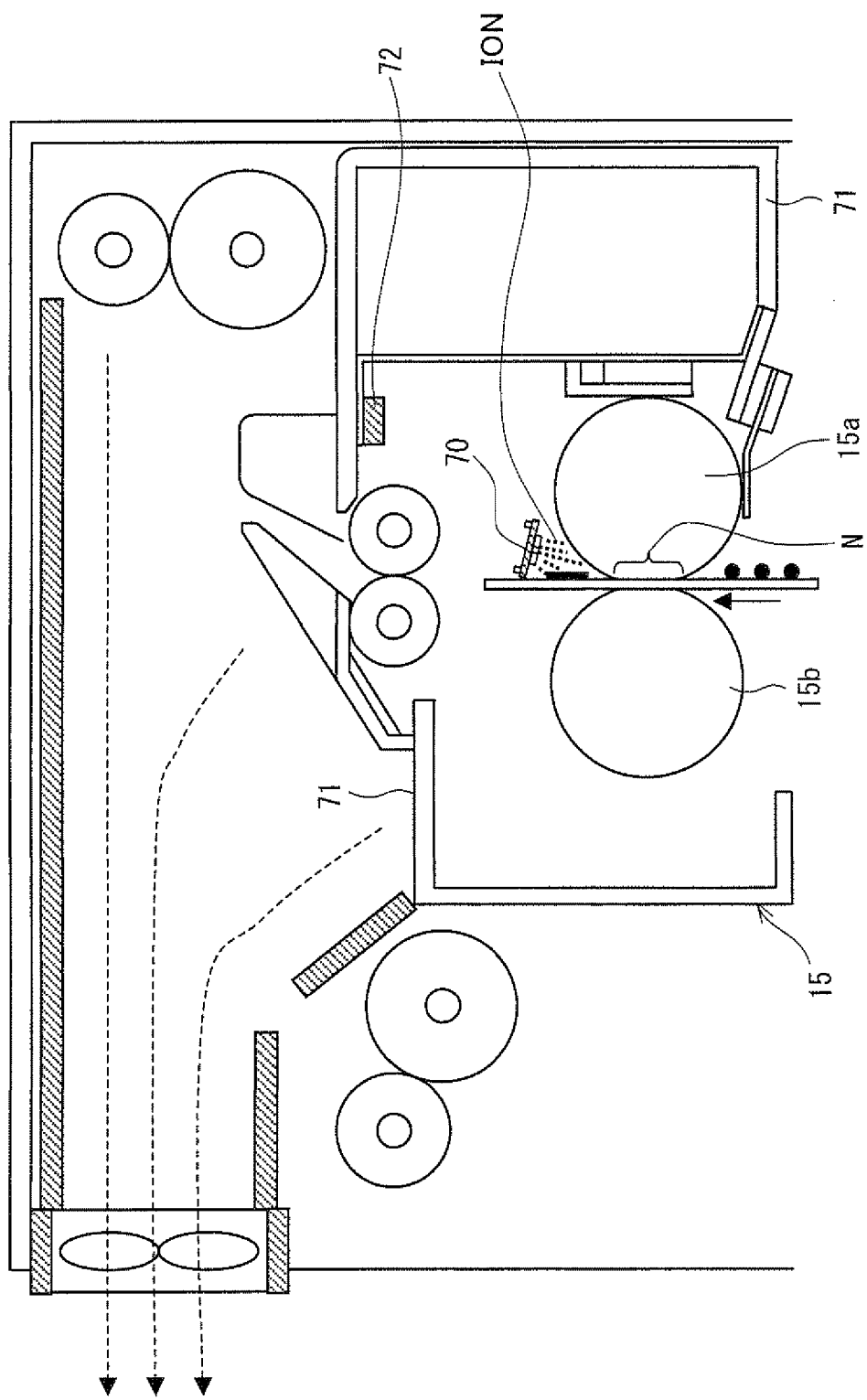
FIG. 28 illustrates a Seventh Embodiment and is a view illustrating the structure of components near a fixing unit.

FIG. 28 is a longitudinal view illustrating the detailed structure of the components around the fixing unit 15 of the present embodiment. The ion generator 70 is arranged within the packaging cover 71 of the fixing unit 15, and adjacent to the fixing roller 15a and the pressure roller 15b being a paired fixing member, so that the generated ions are emitted toward the fixing nip area N where the sheet is discharged.

As illustrated in FIG. 28, the ion generator 70 is preferably arranged in the space on the side of the sheet where the melted and fixed toner image is formed, out of two spaces into which the space above the fixing nip area N is split by the discharged sheet itself. The example of FIG. 28 has the ion generator 70 arranged on the fixing roller 15a side, since the fixing roller 15a is arranged to come into contact with the toner image and melt the toner.

Thus, it is possible to further effectively expose the ion to the chemical emission being generated in the fixing nip area N.

In addition, the ion generator 70 of the present embodiment is of a rectangular shape having an overall length slightly longer (330×8 mm) than the length of the fixing member (320 mm in the present embodiment), so that the ions are emitted towards the whole long sides of the fixing roller 15a and the pressure roller 15b. The ion generator 70 of the surface discharge type is favorable in arranging such long length of the ion generator 60.

In addition, a humidity sensor 72 is provided near the ion generator 70 inside the packaging cover 71 of the fixing unit 15. The amount of ions being generated is adjusted according to the detection result of the humidity sensor 72. Details of this will be described later.

The application of a voltage between the discharge electrode 62 and the induction electrodes 63 of the ion generator 70 (see FIG. 29) causes the generation of the negative ions throughout the whole fixing member. The generated negative ion is then diffused in the downward direction with respect to the ion generator 70, that is, towards the fixing nip area N of the paper discharging side. Thus, the chemical emission being generated in the fixing step is exposed to negative ions.

The main cause for the generation of the volatile organic substance in the electrophotographic image forming apparatus as in the present example is, a siloxane being generated from a silicon oil being used as a mold lubricant in the fixing step or from the heating of a silicon rubber or the like which is used for the fixing roller 15a and the pressure roller 15b. Also, another cause of the volatile organic substance is the VOC or odor component being generated, caused by the heating and melting of the toner in the fixing step. In addition, the reduction effect of the volatile organic substance by the ion improves with a higher humidity.

Thus, the volatile organic substance is more effectively reduced than ever, by arranging the ion generator 70 as illustrated in FIG. 28. That is, the ion generator 70 is arranged such that the ions are emitted towards the sheet discharging side of the fixing nip area N, which is in a high humidity environment caused by the vapor evaporating from the sheet when heated during the fixing step.

In addition, the ion generator 70 of the surface discharge type as illustrated in the present embodiment is small in size, as compared to the ion generators of other type such as the corona discharge type or the electronic discharge type. This enables easy mounting into the fixing unit 15, and also is easily made into a lengthy shape, thereby has the merit that the ions can be emitted towards the whole (sheet) surface of the fixing member.

The ion generator 70 of such surface discharge type has a problem in a high humidity environment that the amount of ions being generated may decrease or become uneven. For example, if the dielectric 61 (see FIG. 29) is mica then the mica itself absorbs moistures, or even if the dielectric 17 is ceramic which is a non-hygroscopic material, condensation forms on the surface of the ceramic. Each of these causes the decrease or unevenness in ion generation.

However, if the ion generator 70 is arranged near the fixing unit 15, the temperature around the ion generator 70 is raised by the heat from the fixing member, preventing moisture absorption. Thus, the amount of ions being generated is stabilized even in a high humidity environment.

In addition, the ion generator 70 of the surface discharge type also has a problem that the amount of ozone generated is greater, as compared to the needle-shaped ion generator of the electronic discharge type. This can also be compensated for by decomposition of ozone due to a high temperature around the fixing section.

Experiment 7

This experiment studied the effect of providing the ion generator 70 inside the fixing unit 15. As in the Experiment 3, the comparative experiments were conducted using the following color multifunction apparatuses: (i) an MX-4500N manufactured by Sharp Corporation provided with the ion generator inside the fixing unit 15 as illustrated in FIG. 28 (Example 4), (ii) an MX-4500N manufactured by same provided with the ion generator 70 inside the duct within the housing (Example 5); (iii) an MX-4500N manufactured by same provided with the ion generator 70 in the vicinity of the paper output opening arranged outside of the housing (Comparative Example 3); and (iv) an MX-4500N manufactured by same without the ion generator 70 being provided (Comparative Example 2).

The present experiment positioned the color multifunction apparatuses of the Examples 4 and 5, Comparative Examples 2 and 3 in a chamber with a capacity of 9.8 m³, and measured the increasing value of odor value inside the chamber when a total of 500 color copies were printed with a print rate of 20% (5% per color) in a speed of 35 sheets per minute. The XP-329III manufactured by New Cosmos Electric Co., Ltd was used for the odor measuring device. In addition, an ac voltage of a rectangular wave of −3 kVpp, 2 kHz was applied to the ion generators 70 of the Examples 4 and 5, and Comparative Examples 3. The result of the experiment is as illustrated in FIG. 30.

Figure 30:
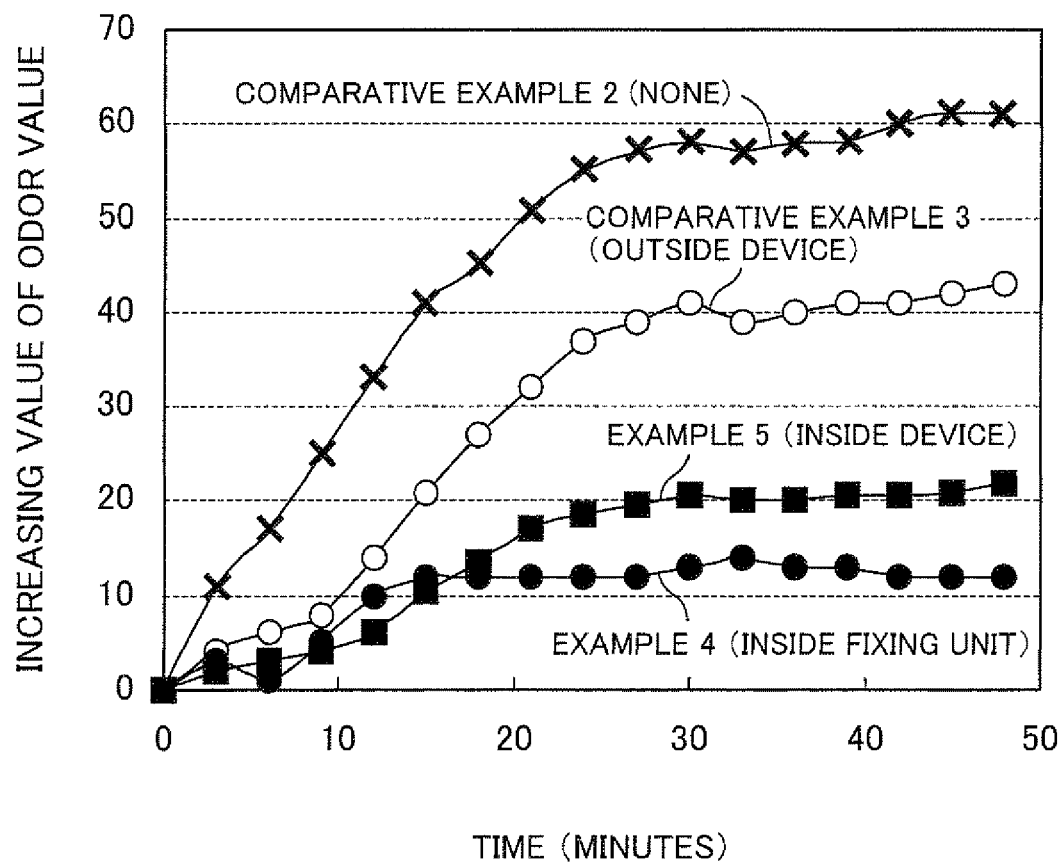
FIG. 30 illustrates the result of Experiment 7, and is a view illustrating relationship between an elapsed time and an increasing value of an odor value.

As illustrated in FIG. 30, it is confirmed that the odor is further reduced with the ion generator 70 provided inside the fixing unit 15, compared to providing the ion generator 70 inside the duct. In addition, the relative humidity in the vicinity of the ion generator 70 during printing was measured using the humidity sensor 72, giving a result as follows:

| | |
|---|---|
| 1. Example 5 (inside duct) | 50% |
| 2. Example 4 (inside fixing unit) | 80% |
| 3. Comparative Example 3 (outside housing) | 50% |

From this, in Example 4, it is considered that the reduction effect of the volatile organic substance by the ion improved due to the high humidity environment in the fixing unit 15, by the water evaporating from the sheet.

In addition, it is found from the result of the Experiment 7 that the reduction effect of the volatile organic substance by the ion differs depending on the humidity. Taking this into account, the present embodiment uses for example the humidity sensor 72 arranged inside the fixing unit 15 to detect the humidity therein, in order to control the amount of ions to be generated in accordance with the humidity.

Specifically, the ion generator 70 further includes a power supply control section (control section) 73 for controlling the high voltage power supply 64 which applies the pulse-shaped driving voltage between the discharge electrode 62 and the induction electrodes 63. The power supply control section 73 controls the high voltage power supply 64 to generate an ac voltage of a predetermined frequency when the output value of the humidity sensor 72 exceeds a predetermined threshold value, and to reduce the frequency of the ac voltage when the output value of the humidity sensor 72 falls below the predetermined threshold value.

More specifically, the power supply control section 72 controls such that a sufficient amount of ions is generated by applying to the ion generator 70 the ac voltage of −3 kVpp, 2 kHx if the humidity is lower than 60%, and if the humidity is 60% or over, the frequency of the ac voltage to be applied to the ion generator 70 is lowered to 1 kHz, to suppress the amount of ions generated to half the amount.

As above, the amount of ions is adjusted in accordance with the humidity. Thus, by generating sufficient amount of ions when the humidity is low, and suppressing the amount of ions being generated when the humidity is high, the deterioration of the ion generation section is prevented, extending the life of the ion generation section, while securely removing the chemical emission.

Experiment 8

Next, an experiment was conducted to study the ozone reduction effect in the case the ion generator 70 was heated and in the case the ion generator 70 was not heated.

The ion generator 70 was an ion generator of a surface discharge type with a dielectric 61 made of mica. The ion generator 70 was arranged in the vicinity of the fixing roller 15a inside the fixing unit 15.

Next, the fixing unit 15 was positioned inside a chamber with a capacity of 1 m³. The amount of ozone generated within the chamber was measured when a predetermined ac voltage (−3 kVpp, 2 kHz) was applied to the ion generator 70, under the following two conditions: (i) a halogen heater (fixing heater) of the fixing unit 15 was OFF; and (ii) the halogen heater of the fixing unit 15 was ON. An Ozone Monitor EG2002F manufactured by Ebara Jitsugyo Co., Ltd. was used as the ozone measuring device, and the ozone concentration within the chamber five minutes after the application of the voltage was measured.

The result of the experiment is as shown in Table 1.

TABLE 1

| | Fixing Heater | Ion Generator Temperature | Amount of Ozone Generated |
|---|---|---|---|
| Comparative Example | OFF | 20° C. | 0.494 ppm |
| Example | ON | 80° C. | 0.957 ppm |

Table 1 shows that when the heater of the fixing unit is turned on, the temperature of the ion generator rises to approximately 80° C. and the amount of ozone is reduced by approximately 48% (from 0.957 to 0.494 ppm). This is because ozone is readily decomposed by heat.

The result confirms the followings: The temperature rises if the ion generator 70 is arranged in the vicinity of the fixing unit 15, creating an environment where the ozone is readily decomposed. This compensates for the drawback of the ion generator 70 of the surface discharge type that a great amount of ozone generates compared to the needle-shaped electrode of the electronic discharge type.

Experiment 9

Next, the present experiment studied the relationship between the ion radiation towards the fixing member by the ion generator 70 and the electrostatic offset occurring in the fixing member.

The testing method of the electrostatic offset is as described below. As in Experiment 6, the ion generator 70 was provided inside the fixing unit 15 of the color multifunction apparatus MX-4500N manufactured by Sharp Corporation as illustrated in FIG. 28. A halftone image (ID 0.75) and a solid image (ID 1.3 or over) of a width 290 mm×20 mm were formed and fixed on the edge section of a sheet (a hammer mill paper of a LT size), in the state where the cleaning member was taken off. Then, the evaluation of the appearance of the toner image after one turn of the fixing roller 15a (approximately 157 mm) was made by visual observation.

In addition, a surface potential of the fixing roller 15a was also measured, using a surface electrometer (Model 1370, manufactured by Trek Incorporated).

TABLE 2

| | Applied Voltage | | Fixing Roller Surface Potential | Electrostatic Offset |
|---|---|---|---|---|
| | Vpp | Frequency | | |
| Comparative Example 1 | — | — | 0 V | X |
| Example 1 | −3 kV | 0.5 kHz | −400 V | Δ |
| Example 2 | −3 kV | 1 kHz | −800 V | ○ |

○: No offset occurred
Δ: Offset occurred (not serious)
X: Offset occurred (serious)

Table 2 shows that the more the ion generator 70 generates the ion, the less the electrostatic offset. The negative ion generated by the ion generator 70 negatively charges the fixing roller 15a, thereby causing an electrostatic repulsive force between the toner (negative charge) and the fixing roller 15a.

No other examples will be illustrated here; however, the ion generator 70 may also be alternated similarly with the ion generator 60', such that a counter electrode is provided. In addition, the power supply control section 72 may also have a function of the power supply control section 29, adjusting the amount of ions generated according to the output value of the odor sensor 28 being provided within the apparatus, as explained in the First Embodiment.

Furthermore, an ion generator being provided inside the fixing unit 15 is preferably an ion generator of a surface discharge type; however, the technology is not limited to this. The ion generator may be an ion generator other than the ion generator of the surface discharge type mentioned in the previous embodiment.

As above, the electronic apparatus is an electronic apparatus which includes a housing and entails the generation of a chemical emission inside the housing, the electronic apparatus further including: an ion generation section generating ions into the atmosphere to remove the chemical emission from the atmosphere, the ion generation section being arranged inside the housing.

Thus, as aforementioned, the chemical emission such as the VOC and odor are sufficiently suppressed, and are further less likely to dirty the outer surface of the electronic apparatus and the surrounding walls thereof.

In addition, the ion generation section is preferably arranged at a position within 100 mm of a chemical emission source.

The amount of ions which is generated by the ion generation section decreases with distance from the ion generation section, and the ions hardly reach to a position 100 mm away. However, the ion generation section is arranged within 100 mm from the chemical emission source, allowing the ions being generated from the ion generation section to react with the chemical emission, which allows effective suppression of the chemical emission.

Specifically, "the ion generation section is arranged at a position within 100 mm of the chemical emission source" means that the distance between the closest ends of the ion generation section and the volatile chemical substance generation source are within 100 mm.

The electronic apparatus preferably further includes an exhaust duct, which is arranged inside the housing, leading an air containing the chemical emission inside the housing to outside of the housing, the ion generation section being arranged inside the exhaust duct.

According to the above arrangement, an exhaust duct is provided for discharging the chemical emission, in which the chemical emission is removed therein. This allows the chemical emission to react with the ion before the chemical emission is diffused, which enables effective removal of the chemical emission.

The electronic apparatus further preferably includes a dust-removing filter which is arranged upstream of the ion generation section in the air passing direction inside the exhaust duct.

Generally, the ion generation section readily decreases in the amount of ions generated due to the effect of dust or the like. However, in the structure of the technology, a filter is arranged upstream of the ion generation section in the direction of the air passing direction, whereby prevents the adhering of the dust to the ion generation section. Thus, the ion generation performance is maintained for a long term.

The ion generation section is preferably arranged such that an ion generating part which generates ions is facing the downstream side of the air passing direction inside the exhaust duct.

As aforementioned, the ion generation section readily decreases in the amount of ions being generated due to dust or the like. However, the ion generation section is arranged such that the ion generating part is facing the downstream side of the air passing direction, whereby can prevent the adhering of the dust or the like to the ion generation section. Thus, the ion generation performance is maintained for a long term.

In addition, the electronic apparatus further includes a power supply applying an alternating voltage, wherein the ion generation section may be an electrode member generating positive ions and negative ions in the atmosphere upon application of an alternating voltage by the power supply.

According to the above arrangement, the electrode member alternatively holds a positive potential and a negative potential when an alternating voltage is applied thereto. As a result, positive ions and negative ions generate in the atmosphere around the electrode member. Many of the chemical emission such as odor and VOC are positively charged; however, some of them are negatively charged. According to the above arrangement, it is possible to effectively remove the chemical emission, regardless of whether the chemical emission is charged positively or negatively.

In addition, the electronic apparatus may be such that the ion generation section includes two ion generation sections, one being a negative ion generation section generating negative ions and the other being a positive ion generation section generating positive ions.

Many of the chemical emission such as odor and VOC are positively charged; however, some of them are negatively charged. According to the above arrangement, both positive ions and negative ions are generated, which allows the effective removal of the chemical emission, regardless of whether the chemical emission is charged positively or negatively.

The negative ion generation section and the positive ion generation section are preferably arranged so as to sandwich the chemical emission source therebetween, or arranged so as to sandwich a flow passage of an air containing the chemical emission inside the housing therebetween.

According to the above arrangement, the negative ions and the positive ions being generated by the respective ion generation sections are attracted towards each other, thereby being led towards the other ion generation section. The chemical emission source or the flow passage of the air containing the chemical emission is present between one ion generation section and the other ion generation section. As such, the generated ions are led towards the chemical emission. Therefore, the suppression effect of the chemical emission is improved.

In addition, the electronic apparatus may further include an exhaust duct, which is arranged inside the housing, leading an air containing the chemical emission inside the housing to outside of the housing, the positive ion generation section and the negative ion generation section being arranged inside the exhaust duct so that, a flow passage of an air inside the exhaust duct is sandwiched between the positive ion generation section and the negative ion generation section.

According to the above arrangement, the flow passage of the air containing the chemical emission is present between one ion generation section and the other ion generation section. Therefore, the generated ions are led towards the chemical emission. Thus, the suppression effect of the chemical emission is improved.

In addition, the ion generation section may generate ions by an electron emmision.

A general ion generator has a needle-shaped discharge electrode and a counter electrode, and generates an ion by generating corona discharge towards the counter electrode (corona discharge scheme). However, this method has the drawback that (1) the amount of ozone generated is extremely large as well as the ions, and (2) the discharge electrode readily deteriorates and is easily dirtied by a corona product. On the other hand, with the arrangement, it is possible to suppress this generation of ozone. Furthermore, the corona product is less likely to adhere to the electrode. Even if the corona product does adhere thereto, cleaning can be performed easily since the adhesion is weak. As such, the ion generation performance is maintained for a long term.

The ion generation section preferably includes an electrode member generating positive or negative ions in the atmosphere upon voltage application; and a counter electrode being arranged to face the electrode member and subjected to application of a voltage opposite in polarity to the ion.

According to the above arrangement, the ion generation section includes a counter electrode which is subjected to application of a voltage opposite in polarity to the generated ion. Therefore, the ion being generated in the atmosphere around the electrode member is attracted towards the counter electrode, generating a strong ion flow. This allows the ions of high concentration to react with the chemical emission, thus enabling effective removal of the chemical emission.

In addition, the ion generation section may include a plate-shaped insulating member; a first planar electrode provided on one surface of the insulating member; and a second planar electrode provided on the other surface of the insulating member, and the ion generation section generates ions upon application of a voltage between the first planar electrode and the second planar electrode.

This is a so-called surface discharge type device. The corona product is less likely to adhere to the electrode, which is of planar structure. Even if the corona product adheres to the electrode, cleaning can be easily conducted.

The electronic apparatus preferably further includes a cleaning section for cleaning the surface of the first planar electrode.

According to the above arrangement, even if the corona product adheres to the first planar electrode, the cleaning section cleans the first planar electrode. Thus, the ion generation performance is maintained for a long term.

In addition, the electronic apparatus further preferably includes a sensor, which is arranged inside the housing, detecting the chemical emission; and a control section controlling the amount of ions being generated from the ion generation section according to a detection result of the sensor.

The art described in Patent Document 1 provides an odor sensor outside the housing, causing difficulty in measuring with high precision when the amount of chemical emission being generated is small. This is because a small amount of the chemical emission immediately diffuses into the atmosphere. Therefore, in order to gain high precision in measurement, the use of an expensive sensor is required.

On the other hand, according to the above arrangement, the sensor is arranged inside the housing. This allows more precise measurement of the chemical emission, as compared to the art of Patent Document 1. Additionally, it is possible to control the ion generation section so as to be turned off when the chemical emission is not detected by the sensor. Thus, the deterioration of the ion generation section is suppressed extending the life thereof, while securely removing the chemical emission.

In addition, the electronic apparatus may have an image formation section forming an image of a sheet (recording medium) with a developer.

An ink used for an inkjet image forming apparatus, or a toner used for an electrophotographic image forming apparatus are chemical emission sources. Therefore, by providing the above-described ion generation section to these image forming apparatus, the chemical emission generating from the developer can be effectively removed.

In addition, the electronic apparatus further preferably includes an adjustment section adjusting the amount of ions being generated by the ion generation section, in accordance with a proportion of an area of an image formed on the sheet in the area of the sheet.

It can be assumed that the increase in the amount of the developer used causes the increase in the amount of chemical emission generated. According to the above arrangement, the amount of ions is adjusted in accordance with a print rate. Therefore, a sufficient amount of ion is generated when the print rate is high, and the ion generation is suppressed when the print rate is low. Thus, the deterioration of the ion generation section is suppressed, extending the life thereof, while securely removing the chemical emission.

In addition, the electronic apparatus may be arranged such that the image forming section includes a fixing section fusing a developer with heat when a sheet (recording medium) passes through a abutting section between a pair of fixing members that are heated and pressed with each other, so as to fix the developer on the sheet, wherein the ion generation section is arranged so that the generated ions are emitted toward the fixing section.

In the electronic apparatus performing image formation by an electrophotographic printing process, the main cause of the generation of the volatile organic substance is: siloxane which generates from the silicon oil being used in the step of fixing the developer onto the sheet or the silicon rubber used as the fixing member; and the VOC and odor components which generate from the developer at the fixing. In addition, the reduction effect of the volatile organic substance by the ion improves with increase in humidity.

As in the above arrangement, the generated ions are emitted towards the fixing section which is highly humid due to vapor evaporating from the sheet heated at the fixing. Thus, the volatile organic substance is more effectively reduced.

In this case, the ion generation section is preferably arranged so that the generated ions are emitted toward an area to which the sheet is discharged through the abutting section between the fixing members.

The ions are directly emitted to the abutting section which is both a generation section of the volatile organic substance and a generation section of the water vapor, both of which create a high humidity environment. Therefore, it is possible to much more effectively reduce the volatile organic substance.

Furthermore, in this case, the fixing section may be provided with a packaging cover in which the ion generation section is arranged.

The packaging cover being provided to the fixing section prevents the diffusing of the volatile organic substance generated at the abutting section, as well as preventing the diffusing of the water vapor. Thus, a high humidity environment is maintained inside the packaging cover. Therefore, with the arrangement in which a packaging cover is provided and the ion generation section is arranged, the volatile organic substance can be much more effectively reduced.

Patent Document 2 (Japanese Unexamined Patent Publication, Tokukaisho, No. 61-275877 (published on Dec. 5, 1986)) discloses an example providing a static eliminator in the vicinity of the fixer, however the fixing scheme of the Patent Document 2 is a flash fixing scheme, and is different to the contact heat fixing scheme adopted by the technology. The feature of the flash fixing scheme is that the toner is melted without heating the sheet as much. Thus, the amount of water vapor generating from the sheet in the fixing section is small, which does not create a high humidity environment even in the vicinity of the fixing section. In addition, the static eliminator is provided on the downstream of the fixing section, and is not arranged such that the generated ions are emitted toward the fixing section.

In addition, Patent Document 1 also discloses an ion generator provided in the vicinity of the fixing section so that the generated ions are inactivated by heat of the fixing section when the ion generator is tourmaline crystal. That is, in Patent Document 1, the ion generator is not provided to attain the effect of raising the reduction rate of the volatile organic substance under a high humidity environment.

Moreover, Patent Document 1 discloses that the generated ions are emitted toward the outside of the apparatus, not towards the fixing section (abutting section) with a higher humidity.

Additionally, the Patent Document 1 describes that the tourmaline crystal is attached on the packaging cover (surface) of the fixer. That is, the temperature outside the packaging cover fixer rises, however the humidity does not rise as much.

The electronic apparatus preferably further includes a humidity sensor, which is arranged in the vicinity of the ion generation section, measuring humidity in an atmosphere; and a control section for controlling the amount of ions generated from the ion generation section according to a measurement result of the humidity sensor.

According to the above arrangement, the amount of ions is adjusted according to humidity. Therefore sufficient amount of ions is generated when the humidity is low, and the amount of the ion to be generated is suppressed when the humidity is high. Thus, while securely removing the chemical emission, deterioration of the ion generation section is prevented, extending the life thereof.

In addition, the electronic apparatus is preferably arranged such that the ion generation section has the same width as the fixing member, and the ion generation section is arranged so the generated ions are emitted toward the overall width of the fixed member.

According to the above arrangement, the electric charges on the surface of the fixing member can also be controlled (to be eliminated therefrom and born thereby) by the ions. Thus, the electrostatic adhering (offset) and scattering of toner in the fixing section can also be prevented, not just the reduction of the volatile organic substance.

In addition, the ion generation section may include a plate-shaped insulating member, a first planar electrode provided on one surface of the insulating member, and a second planar electrode provided on the other surface of the insulating member, wherein the ion generation section generates ions when a voltage is applied to between the first planar electrode and the second planar electrode.

The electrodes in these surface discharge type devices are of planar structure. Therefore, the corona product is less likely to adhere thereto. Even if the corona product does adhere onto the electrode, the corona product is easily cleaned.

These surface discharge type devices particularly are small in size and easy to mount in the fixing unit, as compared to the conventional corona discharge ion generator and electronic discharge ion generator. The surface discharge type devices are also easily made in a lengthy shape, which has the merit that they can emit the ions to the overall width (paper width) of the fixing member.

Furthermore, the surface discharge type devices originally have the problem that the amount of ions generated decreases due to moisture absorption of the insulator (dielectric) or condensation on the surface thereof in a high humidity environment. However, if the device is arranged in the vicinity of the fixing section, the temperature rises due to the heat caused by the fixing, whereby suppresses the moisture absorption. Thus, the amount of ions being generated stabilizes regardless of the environment.

The surface discharge type device has the problem that the amount of ozone generated is greater, as compared to the needle-shaped electronic discharge device. This can also be compensated for by decomposition of ozone due to a high temperature around the fixing section.

The technology is not limited to the description of the embodiments above, but may be altered by a skilled person within the scope of the claims. An embodiment based on a proper combination of technical means disclosed in different embodiments is encompassed in the technical scope.

The embodiments and concrete examples of implementation discussed in the foregoing detailed explanation serve solely to illustrate the technical details, which should not be narrowly interpreted within the limits of such embodiments and concrete examples, but rather may be applied in many variations within the spirit of the technology, provided such variations do not exceed the scope of the patent claims set forth below.

What it claimed is:

1. An image forming apparatus which includes a housing and entails the generation of a chemical emission inside the housing, the electronic apparatus comprising:
    an ion generation section, which is arranged inside the housing, generating ions into an atmosphere to remove the chemical emission from the atmosphere; and
    a power supply applying an alternating voltage,
    the ion generation section generating positive ions and negative ions in the atmosphere upon application of an alternating voltage by the power supply, wherein the positive ions and negative ions generated by the ion generation section react with the chemical emission inside the housing before the chemical emission is discharged and diffused outward from the housing.

2. An image forming apparatus which includes a housing and entails the generation of a chemical emission inside the housing, the electronic apparatus comprising:
    an ion generation section, which is arranged inside the housing, generating ions into an atmosphere to remove the chemical emission from the atmosphere,
    the ion generation section comprising two ion generation sections, one being a negative ion generation section generating negative ions and the other being a positive ion generation section generating positive ions, wherein the positive ions and negative ions respectively generated by the two ion generation sections react with the chemical emission inside the housing before the chemical emission is discharged and diffused outward from the housing.

3. The image forming apparatus as set forth in claim 1, wherein the ion generation section is arranged at a position within 100 mm of a chemical emission source.

4. The image forming apparatus as set forth in claim 1, further comprising:
    an exhaust duct, which is arranged inside the housing, leading an air containing the chemical emission inside the housing to outside of the housing,
    the ion generation section being arranged inside the exhaust duct.

5. The image forming apparatus as set forth in claim 4, further comprising:
    a dust-removing filter which is arranged upstream of the ion generation section in the air flow direction inside the exhaust duct.

6. The image forming apparatus as set forth in claim 4, wherein the ion generation section is arranged such that an ion generating part which generates ions faces the downstream side of the air flow direction inside the exhaust duct.

7. The image forming apparatus as set forth in claim 2, wherein the negative ion generation section and the positive ion generation section are arranged so as to sandwich the chemical emission source therebetween, or arranged so as to sandwich a flow passage of an air containing the chemical emission inside the housing therebetween.

8. The image forming apparatus as set forth in claim 7, further comprising:
    an exhaust duct, which is arranged inside the housing, leading an air containing the chemical emission inside the housing to outside of the housing,
    the positive ion generation section and the negative ion generation section being arranged inside the exhaust duct so that a flow passage of an air inside the exhaust duct is sandwiched between the positive ion generation section and the negative ion generation section.

9. The image forming apparatus as set forth in claim 1, wherein the ion generating section generates ions by electron emission.

10. The image forming apparatus as set forth in claim 1, wherein the ion generation section includes:
    an electrode member generating positive or negative ions in the atmosphere upon voltage application; and
    a counter electrode arranged to face the electrode member and subjected to application of a voltage opposite in polarity to the ion.

11. The image forming apparatus as set forth in claim 1, wherein the ion generation section includes:
    a plate-shaped insulating member;
    a first planar electrode provided on one surface of the insulating member; and
    a second planar electrode provided on the other surface of the insulating member, and the ion generation section generates ions upon application of a voltage between the first planar electrode and the second planar electrode.

12. The image forming apparatus as set forth in claim 11, further comprising: a cleaning section for cleaning the surface of the first planar electrode.

13. The image forming apparatus as set forth in claim 1, further comprising:
    a sensor, which is arranged inside the housing, detecting the chemical emission; and
    a control section controlling an amount of ions being generated from the ion generation section according to a detection result of the sensor.

14. The image forming apparatus as set forth in claim 1, further comprising:

a humidity sensor, which is arranged in the vicinity of the ion generation section, measuring humidity in an atmosphere; and a control section controlling an amount of ions generated from the ion generation section according to a measurement result of the humidity sensor.

* * * * *